United States Patent [19]

Cook et al.

[11] Patent Number: 5,688,941
[45] Date of Patent: Nov. 18, 1997

[54] METHODS OF MAKING CONJUGATED 4' DESMETHYL NUCLEOSIDE ANALOG COMPOUNDS

[75] Inventors: Phillip Dan Cook, Vista; Kelly Teng, San Diego, both of Calif.

[73] Assignee: ISIS Pharmaceuticals, Inc., Carlsbad, Calif.

[21] Appl. No.: 760,848

[22] Filed: Dec. 5, 1996

Related U.S. Application Data

[63] Continuation-in-part of Ser. No. 566,836, Aug. 13, 1990, Pat. No. 5,223,618, and a division of Ser. No. 314,877, Sep. 29, 1994, Pat. No. 5,608,046, which is a continuation-in-part of Ser. No. 39,846, filed as PCT/US92/04294 May 21, 1992, abandoned, which is a continuation-in-part of Ser. No. 903,160, Jun. 24, 1992, abandoned, which is a continuation-in-part of Ser. No. 703,619, May 21, 1991, Pat. No. 5,378, 825, which is a continuation-in-part of Ser. No. 566,836, and Ser. No. 558,663, Jul. 27, 1990, Pat. No. 5,138,045.

[51] Int. Cl.$^6$ ............... C07H 19/06; C07H 19/16; C07H 21/00

[52] U.S. Cl. ............... 536/25.3; 536/23.1; 536/24.3; 536/24.5; 536/25.32; 536/26.1; 536/26.6; 536/27.1

[58] Field of Search ............... 536/22.1, 23.1, 536/24.3, 24.5, 25.3, 25.32, 25.6, 26.1, 26.6, 27.1; 435/6, 375; 514/44

[56] References Cited

U.S. PATENT DOCUMENTS

| | | | |
|---|---|---|---|
| 3,687,808 | 8/1972 | Merigan et al. | 435/91.3 |
| 4,908,453 | 3/1990 | Cocuzza | 548/113 |
| 4,958,013 | 9/1990 | Letsinger | 536/24.5 |
| 5,223,618 | 6/1993 | Cook et al. | 544/276 |
| 5,262,536 | 11/1993 | Hobbs, Jr. | 546/25 |
| 5,391,723 | 2/1995 | Priest | 536/23.1 |
| 5,578,718 | 11/1996 | Cook et al. | 536/27.21 |
| 5,608,046 | 3/1997 | Cook et al. | 536/23.1 |

FOREIGN PATENT DOCUMENTS

| | | |
|---|---|---|
| WO 93/07883 | 4/1993 | WIPO. |
| WO 93/16095 | 8/1993 | WIPO. |
| WO 93/18052 | 9/1993 | WIPO. |
| WO 94/08051 | 4/1994 | WIPO. |

OTHER PUBLICATIONS

Secrist et al., "Synthesis and Biological Activity of 2'-Deoxy-4'-thio Pyrimidine Nucleosides", *J. Med. Chem.*, 1991, 34, 2361-2366.

Smith-Jones et al., "Antibody Labeling with Copper-67 Using the Bifunctional Macrocycle 4-[(1,4,8, 11-Tetraazacyclotetradec-1-yl)methyl]benzoic Acid", *Bioconjugate Chem.*, 1991, 2, 415-421.

Studer et al., "One Step Synthesis of Mono-N-substituted Azamacrocycles with a Carboxylic Group in the Side-Chain and their Complexes with $Cu^{2+}$ and $Ni^{2+}$", *Helvetica Chimica Acta*, 1986, 69, 2081-2086.

Tung et al., "Preparation of Oligonucleotide-Peptide Conjugates", *Bioconjugate Chem.*, 1991, 2, 464-465.

Uhlmann, E. et al., "Antisense Oligonucleotides: A New Therapeutic Principle", *Chem. Rev.*, 1990, 90(4), 543-584.

Uhlmann, E. and Peyman, A., "Oligonucleotide Analogs Containing Dephospho-Internucleoside Linkages", *Methods in Molecular Biology*, Chapter 16 in Protocols for Oligonucleotides and Analogs, S. Agrawal, Ed., The Humana Press, Inc., Totowa, NJ, 1993, 355-389.

Veber, D. F. et al., "Isonicotinyloxycarbonyl, a Novel Amino Protecting Group for Peptide Synthesis", *J. Org. Chem.* 1977, 42(20), 3286-3288.

Zhang, Z. et al., "Uptake of N-(4'-pyridoxyl)amines and Release of Amines by Renal Cells: A Model for Transporter-Enhanced Delivery of Bioactive Compounds", *PNAS USA*, 1991, 88, 10407-10410.

Atherton et al., "The Fluorenylmethoxycarbonyl Amino Protecting Group", Chapter 1 in *The Peptides*, Gross and Meienhofer, Eds., Academic Press, New York, 1983, 9, 1-38.

Bennett et al., "Inhibition of Endothelial Cell Adhesion Molecule Expression with Antisense Oligonucleotides", *J. Immunol.*, 1994, 152, 3530-3540.

Chiang et al., "Antisense Oligonucleotides Inhibit Intercellular Adhesion Molecule 1 Expression by Two Distinct Mechanisms", *J.Biol.Chem.*, 1991, 266, 18162-18171.

Corey and Samuelsson, "One-Step Conversion of Primary Alcohols in the Carbohydrate Series to the Corresponding Carboxylic tert-Butyl Esters", *J. Org. Chem.*, 1984, 49, 4735.

Gait, M.J., ed., *Oligonucleotide synthesis, a practice approach*, IRL Press, 1984, Oxford University Press, New York.

Goodchild, J., "Conjugates of Oligonucleotides and Modified Oligonucleotides: A Review of Their Synthesis and Properties", *Bioconjugate Chem.*, 1990, 1(3), 165-186.

Greene, T.W. and Wuts, P.G.M., *Protective Groups in Organic Synthesis*, 2d. Ed., Wiley & Sons, 1991.

Manoharan, M., *Antisense Research and Applications*, Crooke and Lebleu, eds., CRC Press, Boca Raton, 1993.

Matulic-Adamic et al., "Synthesis of 2'-Deoxy-5-monofluoromethyluridine (FTDR) and 2'-Deoxy-5-difluoromethyluridine ($F_2$TDR)", *J. Chem. Soc., Chem. Comm.*, 1985, 21, 1535-1536.

Meyer et al., "Efficient, Specific Cross-Linking and Cleavage of DNA by Stable, Synthetic Complementary Oligodeoxynucleotides", *J. Am. Chem. Soc.*, 1989, 111, 8517-8519.

Ohlmeyer, M. et al., "Complex synthetic chemical libraries indexed with molecular tags", *Proc. Natl. Acad. Sci. USA*, 1993, 90, 10922-10926.

*Primary Examiner*—George C. Elliott
*Assistant Examiner*—Thomas G. Larson
*Attorney, Agent, or Firm*—Woodcock Washburn Kurtz Mackiewicz & Norris, LLP

[57] ABSTRACT

Tetrahydrofuranyl compounds are provided that are functionalized to include pendant conjugate groups, and which are useful in diagnostic assays and as research reagents. Novel intermediates for the synthesis of the compounds are also provided.

5 Claims, No Drawings

5,688,941

METHODS OF MAKING CONJUGATED 4' DESMETHYL NUCLEOSIDE ANALOG COMPOUNDS

CROSS REFERENCE TO RELATED APPLICATIONS

This application is a division of U.S. Ser. No. 314,877, filed Sep. 29, 1994, which issued Mar. 4, 1997 as U.S. Pat. No. 5,608,046, which is a continuation-in-part of U.S. Ser. No. 039,846, filed as PCT/US92/04294 May 21, 1992, now abandoned, which is a continuation-in-part of U.S. Ser. No. 903,160, filed Jun. 24, 1992, now abandoned, and PCT Application No. U.S. 92/04294, filed May 21, 1992, which both are continuations-in-part of U.S. Ser. No. 703,619, filed May 21, 1991, now U.S. Pat. No. 5,378,825, issued Jan. 3, 1995, which is a continuation-in-part of U.S. Ser. No. 566,836, filed Aug. 13, 1990, now U.S. Pat. No. 5,223,618, issued Jun. 29, 1993 and of U.S. Ser. No. 558,663, filed Jul. 27, 1990, now U.S. Pat. No. 5,138,045, issued Aug. 11, 1992. This application is also a continuation-in-part of PCT Application No. U.S. Ser. No. 91/05713, filed Aug. 12, 1991, which is a continuation-in-part of U.S. Ser. No. 566,836. Each of the foregoing patent applications are assigned to the assignee of this application and are incorporated by reference herein.

FIELD OF THE INVENTION

This invention is directed to oligomeric compounds that are functionalized to include covalently bound groups. Specifically, the oligomeric compounds include a tetrahydrofuran moiety that is functionalized with a pendant conjugate group.

BACKGROUND OF THE INVENTION

Oligonucleotides and their analogs have been developed and used in molecular biology in certain procedures as probes, primers, linkers, adapters, and gene fragments. Modifications to oligonucleotides used in these procedures include labeling with non-isotopic labels, e.g. fluorescein, biotin, digoxigenin, alkaline phosphatase, or other reporter molecules. Other modifications have been made to the ribose phosphate backbone to increase the nuclease stability of the resulting analog. These modifications include use of methyl and other alkyl phosphonates, phosphorothioates, phosphorodithioate, phosphoamidate and phosphotriester linkages, and 2'-O-methyl ribose sugar units. Further modifications include modification made to modulate uptake and cellular distribution. Phosphorothioate oligonucleotides are presently being used in human clinical trials for various disease states, including use as antiviral agents. In view of the success of these oligonucleotides for both diagnostic and therapeutic uses, there exists an ongoing demand for improved oligonucleotide analogs.

Oligonucleotides and like molecules can interact with native DNA and RNA in several ways. One of these is duplex formation between an oligonucleotide and a single stranded nucleic acid. A further method is via triplex formation between an oligonucleotide and double stranded DNA to form a triplex structure.

Naturally occurring or synthetic oligonucleotides, together with hybrid species having both synthetic and natural components, can collectively be referenced as "oligomeric compounds." Because of their properties, these oligomeric compounds are known to be useful in a number of different areas. They can be used as probes in cloning, blotting procedures, and in applications such as fluorescence in situ hybridization (FISH). Also, since local triplex formation inhibits gene transcription, such oligomeric compounds can be used to inhibit gene transcription. Labeled oligomers can also be used to directly map DNA molecules, such as by tagging an oligomer with a fluorescent label and effecting hybridization to complementary sequences in duplex DNA. Oligomers can also be used as identification tags in combinatorial chemical libraries as is disclosed in patent publication WO 94/08051 and Ohlmeyer et al., *Proc. Natl. Acad. Sci. USA*, 1993, 90, 10922–10926.

Considerable research is being directed to the application of oligonucleotides and oligonucleotide analogs that bind complementary DNA and RNA strands for use as diagnostics, research reagents and potential therapeutics.

For most uses, it is desirable to append to oligomeric compounds groups that modulate or otherwise influence their activity or their membrane or cellular transport. One method of increasing such transport is by the attachment of a pendant lipophilic group. U.S. application Ser. No. 117, 363, filed Sep. 3, 1993, entitled "Amine-Derivatized Nucleosides and Oligonucleosides", describes several alkylamino functionalities and their use in the attachment of such pendant groups to oligonucleosides. Additionally, U.S. application Ser. No. 07/943,516, filed Sep. 11, 1992, entitled "Novel Amines and Methods of Making and Using the Same" and corresponding to published PCT application WO 94/06815 describe other novel amine-containing compounds, and their incorporation into oligonucleotides for, inter alia, the purposes of enhancing cellular uptake, increasing lipophilicity, causing greater cellular retention and increasing the distribution of the compound within the cell. U.S. application Ser. No. 08/116,801, filed Sep. 3, 1993, entitled "Thiol-Derivatized Nucleosides and Oligonucleosides", describes nucleosides and oligonucleosides derivatized to include a thioalkyl functionality, through which pendant groups are attached.

Although each of the above-noted patent applications describe useful compounds, there remains a need in the art for additional stable compounds that bind complementary DNA and RNA. There further remains a need in the art for additional methods of attaching pendant groups to oligomeric compounds to further enhance or modulate their binding, cellular uptake, or other activity.

OBJECTS OF THE INVENTION

It is an object of the invention to provide novel nucleosides for use in attaching pendant conjugate groups to oligomeric compounds.

It is a further object of the invention to provide oligomeric compounds that have pendant intercalators, nucleic acid cleaving agents, cell surface phospholipids, diagnostic agents, fluorescent agents and other conjugate groups.

It is yet another object of the invention to provide improvements in research and diagnostic methods and materials for assaying bodily states in animals, especially disease states.

It is a further object of the present invention to provide methods of producing these novel compounds.

These and other objects will become apparent from the following description and accompanying claims.

SUMMARY OF THE INVENTION

The present invention provides compounds useful in diagnostic assays and as research reagents, as well as methods and intermediates for the preparation thereof.

In one aspect of the invention there are provided compounds of structure:

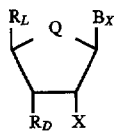

wherein:

$R_L$ is a group of formula:

in which

Z is O, S or HN;

Y is a bivalent linker;

e is 0 or 1;

and $R_C$ is alkyl, alkenyl, alkynyl, O-alkyl, O-alkenyl, O-alkynyl, a polyamine, a polyether, asteroid molecule, a reporter molecule, an aromatic lipophilic molecule, a non-aromatic lipophilic molecule, a reporter enzyme, a peptide, a protein, a water soluble vitamin, a lipid soluble vitamin, a carbohydrate, a terpene molecule, a phospholipid, an intercalator, a cell receptor binding molecule, a crosslinking agent, or a porphyrin;

$B_x$ is a nucleobase;

X is H, OH, O-alkyl, O-alkoxyalkyl, O-alkylamino or F;

Q is O, S, $CH_2$, CHF or $CF_2$; and $R_D$ is H, hydroxyl, an activated phosphorous group, a nucleoside, an activated nucleotide, a nucleotide, an oligonucleotide, an oligonucleoside or a protected derivative thereof.

Compounds are also provided according to the invention having structure:

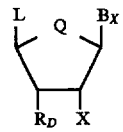

wherein:

L is a group of formula:

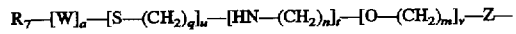

in which

Z is O, S or HN;

t, u and v are each independently integers from 0 to 200;

W is the residue of a linking moiety, said linking moiety being selected from the group consisting of acid chlorides, anhydrides, cyclic anhydrides, alkyl halides, organometallics, chloroformates, isocynates, hydrazines, acids, hydroxylamines, semicarbazides, thiosemicarbazides, hydrazones, hydrazides, trityl thiol, oximes, hydrazide-hydrazones, semicarbazones and semithiocarbazones;

a is 0 or 1;

m, n and q are each independently integers from 1 to 4; and $R_7$ is $R_C$, H or a protecting group; and X, $B_x$, $R_C$ and $R_D$ are defined as above.

In some preferred embodiments t and u are 0, or u and v are zero, or t and v are zero. In other preferred embodiments t and u are 0 and m is 2. In other preferred embodiments t and v are 0 and q is 2, or u and v are 0 and n is 2. In even other preferred embodiments u is 0 and each of t and v are 1, and m and n are each 2.

Also provided according to the invention are compounds of structure:

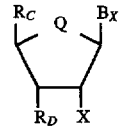

wherein:

$R_C$, $B_x$, X, Q, and $R_D$ are defined as above.

In the above structures, in some preferred compounds, $R_C$ is a polyether or a polyamine. In other preferred embodiments, $R_C$ is asteroid molecule, preferably cholic acid, deoxycholic acid, dehydrocholic acid, cortisone, digoxigenin, testosterone, cholesterol or 3-trimethylaminomethylhydrazido cortisone.

In some preferred embodiments $R_C$ is a water soluble vitamin, preferably thiamine, riboflavin, nicotinic acid, pyridoxal phosphate, pyridoxine, pyridoxamine, deoxypyridoxine, pantothenic acid, biotin, folic acid, 5'-deoxyadenosylcobalamin, inositol, choline or ascorbic acid.

In other preferred embodiments $R_C$ is a lipid soluble vitamin, preferably a retinal, a retinal, retinoic acid, β-carotene, vitamin D, cholecalciferol, a tocopherol, or a phytol.

In some preferred embodiments $R_C$ is a protein, preferably a phosphodiesterase, a peroxidase, a phosphatase or a nuclease. In other preferred embodiments $R_C$ is a reporter molecule, preferably a chromaphore, a fluorophore or a radiolabel-containing moiety. Preferred fluorophores include fluorescein, chrysine, anthracene and perylene.

In some preferred embodiments, X is H, OH, F, O-alkyl having from one to six carbons, O-alkylamino having from one to six carbons or O-alkoxyalkyl having from one to six carbons. In certain more preferred embodiments X is H or OH mimicking natural deoxyribo and ribo sugar analogs. In other more preferred embodiments X is F, O-alkyl having from one to six carbons, alkylamino having from one to six carbons or O-alkoxyalkyl having from one to six carbons such that the compounds are homologous to certain nucleotide species that have either greater nuclease resistance or high binding affinity.

In other preferred embodiments, $R_D$ is H or OH; or $R_D$ is an activated phosphorous group, or $R_D$ is an oligonucleotide.

The present invention also provides novel synthons useful for the preparation of monomeric and polymeric conjugate compounds. In some embodiments these synthons have the structure:

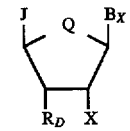

wherein J is a leaving group and Q, $R_D$, $B_x$ and X are as defined above. Preferably, J is OH, SH, $NH_2$, trifluoromethylsulfonyl, methylsulfonyl, halogen, O-trichloroacetimidate, acyloxy, dialkyl phosphite, 2,4,6-trichlorophenyl, p-toluenesulfonyl, 4-dimethylaminoazobenzenesulfonyl or 5-dimethylaminonaphthalenesulfonyl.

Also provided are methods for forming a 5'-desmethyl conjugate oligomer having structure:

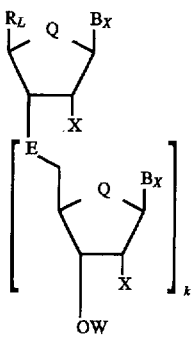

Preferred methods comprise the steps of:
(a) providing a first synthon having structure:

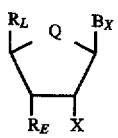

and (b) contacting the first synthon with a second synthon having structure:

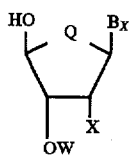

for a time and under reaction conditions sufficient to form the conjugated oligomer; wherein $R_E$ is an activated phosphorous group, W is H or a hydroxyl protecting group, k is an integer from 0 to 50, E is a phosphorous linking species including phosphodiester, phosphotriester, phosphorothioate, phosphorodithioate, alkyl phosphonates especially methyl phosphonates and phosphoramidates phosphorous linking groups, and Q, $R_L$, $B_x$ and X are as defined above.

The present invention also provides methods for forming a 5'-desmethyl conjugated monomer having structure:

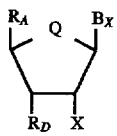

In certain embodiments these methods comprise the steps of providing a synthon having structure:

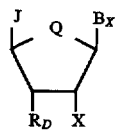

and contacting this synthon with an activated conjugating group. This contacting should be for a time and under reaction conditions sufficient to form the conjugated oligomer. Preferably, J is OH, SH, NH$_2$, trifluoromethylsulfonyl, methylsulfonyl, halogen, O-trichloroacetimidate, acyloxy, dialkyl phosphite, 2,4,6-trichlorophenyl, p-toluenesulfonyl, 4-dimethylaminoazobenzenesulfonyl or 5-dimethylaminonaphthalenesulfonyl; more preferably trifluoromethylsulfonyl, methylsulfonyl, halogen or acyloxy.

DETAILED DESCRIPTION OF PREFERRED EMBODIMENTS

The present invention provides novel nucleosides for incorporation into nucleic acids. In one aspect, the invention provides nucleosides bearing pendant conjugate groups.

The term "nucleoside" refers to a unit composed of a heterocyclic base and a sugar, generally a pentose sugar. In naturally occurring nucleosides, the heterocyclic base typically is guanine, adenine, cytosine, thymine or uracil, and the sugar is normally deoxyribose, i.e., erythropentofuranosyl, or ribose, i.e., ribopentofuranosyl. Synthetic sugars also are known, including arabino, xylo or lyxo pentofuranosyl sugars and hexose sugars. Further synthetic sugar are the 4'-deoxy-4'-thio sugars (both 2'-deoxy and ribo varieties) that have been described by Secrist et al., *J. Med. Chem.* 1991, 34, 2361–2366 and patent application PCT/FR93/00115, respectively, (whereby Q in the above structures is S). Throughout this specification, reference to the sugar portion of a nucleoside or other nucleic acid species shall be understood to refer to naturally occurring deoxyribose and ribose sugars and also to sugar species which can replace the sugar moieties of naturally occurring nucleic acids.

Reference to the nucleobase or heterocyclic base portion of a nucleoside or other nucleic acid species shall be understood to refer to naturally-occurring nucleobases, modified derivatives thereof, or to synthetic nucleobases. Synthetic nucleobases are those which can replace one or more of the naturally occurring base moieties of wild type nucleic acids.

Reference to inter-sugar linkages shall be taken to include moieties that join the sugar portions of nucleosides or nucleotides.

The term "nucleotide" refers to a nucleoside having a phosphate group esterified to one of its 2', 3' or 5' sugar hydroxyl groups. The phosphate group normally is a monophosphate, diphosphate or triphosphate.

The term "oligonucleotide" refers to a plurality of monophosphate nucleotide units that are typically formed from naturally occurring bases and pentofuranosyl sugars joined by native phosphodiester bonds in a specific sequence. A homo-oligonucleotide is formed from nucleotide units having the same heterocyclic base, e.g. polyadenosine.

The term "oligonucleotide analog" has been used in various published patent application specifications and other literature to refer to molecular species that are similar to oligonucleotides, but that have non-naturally occurring portions. This term has been used to identify oligonucleotide-like molecules that have altered sugar moieties, altered base moieties or altered inter-sugar linkages. Thus, the term oligonucleotide analog has been used to denote structures having altered inter-sugar linkages including phosphorothioate, phosphorodithioate, methyl phosphonate, phosphotriester or phosphoramidate inter-nucleoside linkages in place of phosphodiester inter-nucleoside linkages; purine and pyrimidine heterocyclic bases other than guanine, adenine, cytosine, thymine or uracil and sugars having other than the β pentofuranosyl configuration or sugars having substituent groups at their 2' position or substitutions for one or more of the hydrogen atoms. The term "modified oligonucleotide" also has been used in the literature to denote such structures.

The term "oligonucleotide mimic" has also been used to refer to macromolecular moieties that function similarly to or "mimic" the function of oligonucleotides but have non-naturally occurring inter-sugar linkages. Oligonucleotide mimics thus can have natural or altered or non-naturally occurring sugar moieties and natural or altered or non-naturally occurring base moieties in combination with non-naturally occurring dephospho linkages. Certain dephospho linkages have been reviewed by Uhlmann, E. and Peyman, A., "Oligonucleotide Analogs Containing Dephospho Internucleoside Linkages" in Methods in Molecular Biology, Chapter 16, Oligonucleotide Synthetic Protocols, S. Agrawal, Ed., The Humana Press, Inc., Totowa, N.J., 1993.

The term "oligomers" is intended to encompass oligonucleotides, oligonucleotide analogs, oligonucleosides or oligonucleotide-mimicking macromolecules. Thus, "oligomers" refers to nucleosides or nucleoside analogs that are joined together via either natural phosphodiester bonds or via other linkages.

In certain embodiments the nucleoside compounds of the invention lack the 5'-methylene group present in conventional pentofuranosyl nucleosides. In certain preferred embodiments a heteroatom occupies the position normally occupied by the missing 5'-methylene group. In one sense, these compounds can be considered as 4'-desmethyl pentofuranosyl nucleosides. However, in accordance with IUPAC rules, the lack of a 5'-methylene carbon on the "sugar portion" of the nucleosides of the invention require their designation as tetrahydrofuranyl moieties. Thus, in naming these compounds according to IUPAC rules, as for example in the identification of the structural positions of the compound, established hierarchical or priority nomenclature rules are followed. Accordingly, in embodiments wherein a heteroatom has replaced the 5'-methylene group, that heteroatom and the pendant conjugate group attached thereto takes priority over the heterocyclic base of the nucleoside. In such structures, the tetrahydrofuranyl ring is numbered counterclockwise and the position occupied by the heteroatom (in what would be the 5' position of a conventional nucleoside) is identified as the 2-position. However, in identifying certain of the protons in the NMR spectra, conventional pentofuranosyl nucleoside numbering has been used (except where otherwise noted) for the tetrahydrofuranyl nucleosides.

For the purpose of this specification and the claims appended hereto, when an oligomeric structure of the invention is being considered, the ends of this structure are referenced in the same manner as for conventional oligonucleotides. Thus, they are identified either as a 3' end or a 5' end. In other instances where analogy to conventional pentofuranosyl nucleosides is made, strict IUPAC naming rules are deviated from and the numbering system of the conventional pentofuranosyl nucleosides is maintained. In these instances it is convenient to consider certain tetrahydrofuranyl compounds more as 4'-desmethyl pentofuranosyl compounds and thus attachment is noted as being at the 4' position.

Compounds of the invention include 4'-desmethyl nucleoside monomers modified to bear conjugate groups on their 4'-carbons (i.e., 4'-desmethyl conjugate monomers) or oligomers which contain such modified nucleosides (4'-desmethyl conjugate oligomers). Some oligomeric embodiments have the structure:

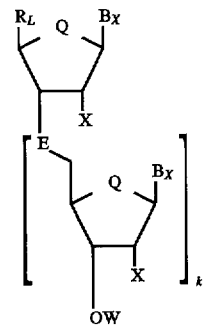

wherein a pendant conjugate group $R_L$ is attached to the 4'-position of a nucleoside of the invention. In this structure the "E" group can be any of the commonly use oligonucleotide phosphorous linkage including phosphodiester, phosphotriester, phosphorothioate, phosphorodithioate, alkyl phosphonate and phosphoamidate linkages. The pendant conjugate group can be a group of formula:

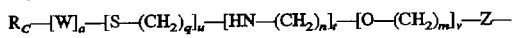

wherein Z is O, NH or S, preferably O or NH, t, u and v are each independently integers from 0 to 200; m, n and q are each independently integers from 1 to 4; W is the residue of a linking moiety, said linking moiety being selected from the group consisting of acid chlorides, anhydrides, cyclic anhydrides, alkyl halides, organometallics, chloroformates, isocynates, hydrazines, acids, hydroxylamines, semicarbazides, thiosemicarbazides, hydrazones, hydrazides, trityl thiol, oximes, hydrazide-hydrazones, semicarbazones and semithiocarbazones;

a is 0 or 1; and $R_C$ is alkyl, alkenyl, alkynyl, O-alkyl, O-alkenyl, O-alkynyl, a polyamine, a polyether, asteroid molecule, a reporter molecule, an aromatic lipophilic molecule, a non-aromatic lipophilic molecule, a reporter enzyme, a peptide, a protein, a water soluble vitamin, a lipid soluble vitamin, a carbohydrate, a terpene molecule, a phospholipid, an intercalator, a cell receptor binding molecule, a crosslinking agent, an RNA cleaving complex, a metal chelator, an alkylator or a porphyrin.

In oligomers of the invention at least one 4'-desmethyl nucleoside unit incorporated therein has been derivatized to bear a pendant conjugate group as described above. When so derivatized, the oligomeric compound is useful, for example, in a diagnostic or other preparation that includes a nucleic acid binding agent to assist in identification of the oligomeric compound, to aid in transfer of the compound across cellular membranes, or to impart other properties. Such a diagnostic or nucleic acid binding agent is formed from an oligomeric compound of the invention wherein the oligomeric compound includes monomeric units bearing natural or non-natural occurring bases in a sequence that is complementary to and will specifically hybridize with a region of an RNA or DNA of interest.

For the purpose of identification, a functionalized oligomeric compound according to the invention can be characterized as a substituent-bearing (e.g., steroid-bearing) oligomeric compound. Such oligomeric compounds will have at least one pendant group attached thereto to modulate their activity.

The compounds of the inventions have various uses including being useful as research reagents and in diagnostic assays. In one particular diagnostic assay, compounds of the inventions are used to isolate the effects of one cellular adhesion molecule from those of a further cellular adhesion molecule in a protein expression assay. In this assay, the effect of induced expression of intercellular adhesion molecule-1 (ICAM-1) were diminished while those of VCAM-1 were maintained. This allows for analysis of the VCAM-1 protein expression without concurrent expression and interference of ICAM-1 protein.

In general, the oligomeric compounds bearing pendant conjugate groups of the present invention can be used to bind to various other target molecules. Target molecules of the present invention can include any of a variety of biologically significant molecules. Other such target molecules can be nucleic acids, carbohydrates, glycoproteins or other proteins.

In binding to nucleic acids, the functionalized oligomeric compounds of the invention bind with complementary strands of RNA or DNA. After binding, the oligomeric compound and the RNA or DNA strand can be considered to be complementary strands which are "duplexed" in a manner analogous to native, double-stranded DNA. In such complementary strands, the individual strands are positioned in such a manner with respect to one another so as to allow Watson-Crick type, Hoogsteen type or another type hybridization of the heterocyclic bases of one strand to the heterocyclic bases of the opposing strand.

Binding to nucleic acids can be practiced against nucleic acids from a variety of sources including organisms ranging from unicellular prokaryotes and eukaryotes to multicellular eukaryotes. The nucleic acid from any organism that utilizes DNA-RNA transcription or RNA-protein translation as a fundamental part of its hereditary, metabolic or cellular control is susceptible to such binding. Seemingly diverse organisms such as bacteria, yeast, virus, protozoa, algae, all plant and all higher animal forms, including warm-blooded animals, are sources of such nucleic acid. Further, since each of the cells of multicellular eukaryotes includes both DNA-RNA transcription and RNA-protein translation as an integral part of their cellular activity, nucleic acid binding for various purposes, e.g. diagnostics, can also be practiced on such cellular populations. Furthermore, many of the organelles, e.g., mitochondria and chloroplasts, of eukaryotic cells include transcription and translation mechanisms. Thus, single cells, cellular populations or organelles can also be included within the definition of organisms that are capable of being treated with nucleic acid binders. In some preferred embodiments of the present invention, the target molecule is a protein such as an immunoglobulin, receptor, receptor binding ligand, antigen or enzyme and more specifically can be a phospholipase, tumor necrosis factor, endotoxin, interleukin, plasminogen activator, protein kinase, cell adhesion molecule, lipoxygenase, hydrolase or transacylase. In other embodiments of the invention the target molecules can be important regions of the human immunodeficiency virus, Candida, herpes viruses, papillomaviruses, cytomegalovirus, rhinoviruses, hepatitis viruses, or influenza viruses. In further embodiments, the target molecules can be regions of an oncogene. In still further embodiments, the target molecule is ras 47-mer stem loop RNA, the TAR element of human immunodeficiency virus or the gag-pol stem loop of human immunodeficiency virus (HIV). Still other targets can induce cellular activity. For example, a target can induce interferon.

Binding also can be practiced against transcription factors. In binding to transcription factors or other target molecules, the transcription factor or other target molecule need not be purified. It can be present, for example, in a whole cell, in a humoral fluid, in a crude cell lysate, in serum or in other humoral or cellular extracts. Of course, purified transcription factor or a purified form of another target molecule is also useful in some aspects of the invention.

In still other embodiments of the present invention, synthetically prepared transcription factors or other target molecules can be useful. A transcription factor or other target molecule also can be modified, such as by biotinylation or radiolabeling. For example, a synthetically prepared transcription factor can incorporate one or more biotin molecules during synthesis or can be modified postsynthesis.

Transcription factors, as the term is used herein, are DNA- or RNA-binding proteins that regulate the expression of genes. HIV tat and c-rel are examples of transcription factors which regulate the expression of genes. Also encompassed by the term are DNA and RNA binding proteins which are not strictly considered transcription factors, but which are known to be involved in cell proliferation. These transcription factors include c-myc, fos, and jun. Methods of the present invention are particularly suitable for use with transcription factors as target molecules since transcription factors generally occur in very small cellular quantities.

In still other embodiments of the invention, nucleic acid binding can be used to treat objects (glasswares, petri dishes, instruments or the like) to sterilize, sanitize or disinfect such objects that may harbor an organism, e.g., bacterial, protozoan, viral, fungal or other infectious or non-infectious agent on the object. In binding to the nucleic acid of the agent, the compounds of the invention will kill, abrogate, inhibit, curtail or other wise control, eradicate or render harmless the cellular growth or gene expression of such organisms on the object. Such nucleic acid binding can also be used to render such organisms incapable or otherwise unable to reproduce themselves.

In still further embodiments of the inventions, the nucleic acid binding properties of the compounds of the invention can be used to form duplex structures with an unknown oligomer species for identification of that species by gel analysis including slab and capillary gel electrophoresis. In still further embodiments of the inventions, the compounds of the invention can be used as tags in identification of other compounds in combinatorial libraries.

Preferred nucleobase units for oligomeric compounds of the invention include naturally occurring or synthetic purine or pyrimidine heterocyclic bases, including but not limited to adenine, guanine, cytosine, thymine, uracil, 5-methylcytosine, hypoxanthine or 2-aminoadenine. Other such heterocyclic bases include 2-methylpurine, 2,6-diaminopurine, 6-mercaptopurine, 2,6-dimercaptopurine, 2-amino-6-mercaptopurine, 5-methylcytosine, 4-amino-2-mercaptopyrimidine, 2,4-dimercaptopyrimidine and 5-fluorocytosine. Representative heterocyclic bases are disclosed in U.S. Pat. No. 3,687,808 (Merigan, et al.), which is incorporated herein by reference.

In preferred embodiments, the oligomeric compounds of the invention include from about 2 to about 50 nucleoside subunits (i.e., k=about 1 to about 49).

As used in this specification, alkyl groups of the invention include but are not limited to $C_1$–$C_{12}$ straight and branched chained alkyls such as methyl, ethyl, propyl, butyl, pentyl, hexyl, heptyl, octyl, nonyl, decyl, undecyl, dodecyl, isopropyl, 2-butyl, isobutyl, 2-methylbutyl, isopentyl, 2-methylpentyl, 3-methylpentyl, 2-ethylhexyl and 2-propylpentyl. Alkenyl groups include but are not limited to unsaturated moieties derived from the above alkyl groups including but not limited to vinyl, allyl and crotyl. Alkynyl groups include unsaturated moieties having at least one triple bond that are derived from the above alkyl groups including but are not limited to ethynyl and propargyl. Alkanoyl groups according to the invention are alkyl, alkenyl or alkynyl groups attached through a carbonyl group.

The term aryl is intended to denote monocyclic and polycyclic aromatic groups including, for example, phenyl, naphthyl, xylyl, pyrrole, and furyl groups. Although aryl groups (e.g., imidazo groups) can include as few as 3 carbon atoms, preferred aryl groups have 6 to about 14 carbon atoms, more preferably 6 to about 10 carbon atoms. Aralkyl and alkaryl groups according to the invention each include alkyl and aryl portions. Aralkyl groups are attached through their alkyl portions, and alkaryl groups are attached through their aryl portions. Benzyl groups provide one example of an aralkyl group, and p-tolyl provides an example of an alkaryl group.

Alkylamino and aminoalkyl groups according to the invention each include amino and alkyl portions. Alkylamino groups are attached through their amino portions, and aminoalkyl groups are attached through their alkyl portions. Methylamino groups provide one example of an alkylamino group, a β-aminobutyl group is one example of an aminoalkyl group.

The terms alkyl, alkaryl, aralkyl and aryl are intended to denote both substituted (e.g., halogenated and hydroxylated) and unsubstituted moieties.

Halogens include fluorine, chlorine and bromine.

Suitable heterocyclic groups include but are not limited to imidazole, tetrazole, triazole, pyrrolidine, piperidine, piperazine and morpholine. Heterocycloalkyl groups are cyclic alkyl groups containing a heretoatom. Heterocycloalkaryl groups are aryl heterocycles bearing at least one alkyl substituent.

Amines include amines of all of the above alkyl, alkenyl and aryl groups including primary and secondary amines and "masked amines" such as phthalimide. Amines are also meant to include polyalkylamino compounds and aminoalkylamines such as aminopropylamine and further heterocycloalkylamines such as imidazol-1, 2 or 4-yl-propylamine.

Substituent groups for the above as well as for other moieties listed below include but are not limited to other alkyl, haloalkyl, alkenyl, alkynyl, alkoxy, thioalkoxy, haloalkoxy and aryl groups as well as halogen, hydroxyl, amino, azido, carboxy, cyano, nitro, mercapto, sulfides, sulfones, sulfoxides, keto, carboxy, nitrates, nitrites, nitroso, nitrile, trifluoromethyl, O-alkyl, S-alkyl, NH-alkyl, amino, silyl, amides, ester, ethers, carbonates, carbamates, ureas, imidazoles, intercalators, conjugates, polyamines, polyamides, polyethylene glycols, polyethers, groups that enhance the pharmacodynamic properties of oligonucleotides, and groups that enhance the pharmacokinetic properties of oligonucleotides. Other suitable substituent groups also include rhodamines, coumarins, acridones, pyrenes, stilbenes, oxazolopyridocarbazoles, anthraquinones, phenanthridines, phenazines, azidobenzenes, psoralens, porphyrins and cholesterols. One particularly preferred group is $CF_3$.

As used in the present invention, the term polyether means a linear or branched alkyl chain periodically interrupted by oxygen atoms. One preferred example of a polyethers is polyethylene glycol. The term polyamine as used herein includes the nitrogen analogs of such structures, and the term polythioether includes the sulfur analogs of such structures.

Carbohydrates according to the invention are inclusive of pentose, hexose and higher sugars, and the polymeric species thereof. Representative carbohydrates include glucose and galactose and their derivatives including, as for example, glycals, glycal epoxides and glycosides.

Terpenes are known in the art as oligomers of isoprene, particularly the dipentenes, pinenes, and myrcenes. Included within the definition of terpene molecules are terpene derivatives such as camphor and menthol.

The term phospholipid as used herein includes those compounds which upon hydrolysis yield phosphoric acid, an alcohol and one or more fatty acids. Representative examples of phospholipids include lecithin, cephalin and sphingomyelin.

As used in the present invention, groups that enhance the pharmacodynamic properties include groups that improve oligonucleotide uptake, enhance oligonucleotide resistance to degradation, and/or strengthen sequence-specific hybridization with RNA. Groups that enhance the pharmacokinetic properties, in the context of this invention, include groups that improve oligonucleotide uptake, distribution, metabolism or excretion.

For the purposes of this invention, the terms "reporter molecule" and "reporter enzyme" are inclusive of those molecules or enzymes that have physical or chemical properties that allow them to be identified in gels, fluids, whole cellular systems, broken cellular systems and the like utilizing physical properties such as spectroscopy, radioactivity, colorimetric assays, fluorescence, and specific binding. Particularly useful as reporter molecules are fluorophores, chromaphores and radiolabel-containing moieties. Fluorophores are molecules detectable by fluorescence spectroscopy. Examples of preferred fluorophores are fluorescein and rhodamine dyes and acridines. There are numerous commercial available fluorophores including "Texas Red" and other like fluoresceins and rhodamines available for Molecular Probes, Eugene, OR. Chromaphores are molecules capable of detection by visible or ultraviolet (UV-VIS) absorbance spectroscopy. Examples of chromaphores are polynuclear aromatics such as anthracene, perylene, pyrene, rhodamine and chrysene. Radiolabel-containing moieties, as used herein, are molecules incorporating at least one radioactive atom, such as $^3H$ or $^{14}C$, enabling detection thereby. Reporter enzymes may be detected directly or via their enzymatic products by any of the methods mentioned above. Particularly useful as reporter enzymes are alkaline phosphatase and horseradish peroxidase.

Steroid molecules according to the invention include those chemical compounds that contain a perhydro-1,2-cyclopentanophenanthrene ring system. Particularly useful as steroid molecules are the bile acids including cholic acid, deoxycholic acid and dehydrocholic acid; steroids including cortisone, digoxigenin, testosterone and cholesterol and cationic steroids such as cortisone having a trimethylaminomethyl hydrazide group attached via a double bond at the 3-position of the cortisone ring (3-trimethylaminomethylhydrazido cortisone).

Proteins and peptides are utilized in their usual sense as polymers of amino acids. Normally peptides comprise such polymers that contain a smaller number of amino acids per unit molecule than do the proteins. Particularly useful as peptides and proteins are sequence-specific peptides and proteins including phosphodiesterases, peroxidases, phosphatases and nucleases. Such peptides and proteins include, but are not limited to, SV40 peptide, RNase A, RNase H and Staphylococcal nuclease.

Lipophilic molecules include naturally-occurring and synthetic aromatic and non-aromatic moieties such as fatty acids, esters and alcohols, other lipid molecules, cage structures such as adamantane and buckminsterfullerenes, and aromatic hydrocarbons such as benzene, perylene, phenanthrene, anthracene, naphthalene, pyrene, chrysene, and naphthacene. Particularly useful as lipophilic molecules are alicyclic hydrocarbons, saturated and unsaturated fatty acids, waxes, terpenes and polyalicyclic hydrocarbons including adamantane and buckminsterfullerenes.

Alkylators according to the invention are moieties that can effect attachment of electrophilic groups to targeted molecular structures. Representative alkylators are disclosed by Meyer, et al., *J. Am. Chem. Soc.* 1989, 111, 8517.

Intercalators are polycyclic aromatic moieties that can insert between adjacent base pairs without affecting normal Watson-Crick base pairing, and include hybrid intercalator/ligands such as the photonuclease/intercalator ligand 6-[[[9-[[6-(4-nitrobenzamido)hexyl]amino]acridin-4-yl]carbonyl]amino]hexanoylpentafluorophenyl ester. This compound has two noteworthy features: an acridine moiety that is an intercalator and a p-nitrobenzamido group that is a photonuclease. Other representative intercalators are disclosed by Manoharan, M., *Antisense Research and Applications*, Crooke and Lebleu, eds., CRC Press, Boca Raton, 1993.

Cell receptor binding molecules according to the invention are vitamins and carbohydrate moieties for which specific receptors exist within a cell. Representative cell receptor binding molecules are disclosed by application Ser. No. PCT/US92/09196, filed Oct. 23, 1992, the contents of which are incorporated herein by reference.

Crosslinking agents are moieties that can effect intrastrand or interstrand covalent binding of RNA and/or DNA, and include photo-crosslinking agents. Examples of photo-crosslinking agents include aryl azides such as N-hydroxysuccinimidyl-4-azidobenzoate (HSAB) and N-succinimidyl-6(-4'-azido-2'-nitrophenylamino)hexanoate (SANPAH). Aryl azides conjugated to oligomers will effect crosslinking with nucleic acids and proteins upon irradiation. Other representative crosslinking agents are disclosed in International patent application Ser. No. PCT/US93/02059, filed Mar. 5, 1993, which is incorporated herein by reference.

Useful crown amines are disclosed by Studer, et al., *Helv. Chim. Acta* 1986, 69, 2081 and Smith-Jones, et al., *Bioconjugate Chem.* 1991, 2, 415.

Vitamins according to the invention generally can be classified as water soluble or lipid soluble. Water soluble vitamins include thiamine, riboflavin, nicotinic acid or niacin, the vitamin $B_6$ pyridoxal group, pantothenic acid, biotin, folic acid, the $B_{12}$ cobalamin coenzymes, inositol, choline and ascorbic acid. Lipid soluble vitamins include the vitamin A family, vitamin D, the vitamin E tocopherol family and vitamin K (and phytols). The vitamin A family, including retinoic acid and retinol, are absorbed and transported to target tissues through their interaction with specific proteins such as cytosol retinol-binding protein type II (CRBP-II), Retinol-binding protein (RBP), and cellular retinol-binding protein (CRBP). These proteins, which have been found in various parts of the human body, have molecular weights of approximately 15 kD. They have specific interactions with compounds of the vitamin A family, especially, retinoic acid and retinol.

The vitamin A family of compounds can be attached to oligomers of the invention via acid or alcohol functionalities found in the various family members. For example, conjugation of an N-hydroxysuccinimide ester of an acid moiety of retinoic acid to an amine function of a pendant group of the oligomer results in linkage of the vitamin A compound to the oligomer, via an amide bond. In similar fashion, standard esterification chemistries may be used to attach the acid moiety of the retinoic acid group to a 4'-oxygen of a compound of the invention, or to a hydroxyl function of a pendent group thereof.

α-Tocopherol (vitamin E) and other tocopherols (beta through zeta) can be similarly conjugated to oligomers also to enhance uptake due to their lipophilic character. The lipophilic vitamin, vitamin D, and its ergosterol precursors can be conjugated to oligomers through their hydroxyl groups by first activating the hydroxyl groups by forming, for example, hemisuccinate esters. Conjugation then is effected, as for instance, to an aminolinker pendant from the oligomer, or through other suitable functional groups described herein. Other vitamins that can be conjugated to oligomers through hydroxyl groups on the vitamins include thiamine, riboflavin, pyridoxine, pyridoxamine, pyridoxal, deoxypyridoxine. Lipid soluble vitamin K's and related quinone-containing compounds can be conjugated via carbonyl groups on the quinone ring. The phytol moiety of vitamin K may also serve to enhance binding of the oligomers to cells.

Pyridoxal phosphate is the coenzyme form of Vitamin $B_6$. Vitamin $B_6$ is also known as pyridoxine. Pyridoxal has specific $B_6$-binding proteins. The role of these proteins in pyridoxal transport has been studied by Zhang and McCormick, *Proc. Natl. Acad. Sci. USA*, 1991 88, 10407. Zhang and McCormick showed that a series of N-(4'-pyridoxyl)amines, in which several synthetic amines were conjugated at the 4'-position of pyridoxal, were able to enter cells by a process facilitated by the $B_6$ transporter. Zhang and McCormick also demonstrated the release of these synthetic amines within the cell. Other pyridoxal family members include pyridoxine, pyridoxamine, pyridoxal phosphate, and pyridoxic acid. Pyridoxic acid, niacin, pantothenic acid, biotin, folic acid and ascorbic acid can be conjugated to oligomers using N-hydroxysuccinimide esters as described above for retinoic acid.

Other groups for modifying properties of oligomers include RNA cleaving complexes, pyrenes, metal chelators, porphyrins, alkylators, hybrid intercalator/ligands and photo-crosslinking agents. RNA cleavers include o-phenanthroline/Cu complexes and Ru(bipyridine)$_3^{2+}$ complexes. The Ru(bipyridine)$_3^{2+}$ complexes interact with nucleic acids and cleave nucleic acids photochemically. Metal chelators include EDTA, DTPA, and o-phenanthroline. Alkylators include compounds such as iodoacetamide. Porphyrins include porphine, its substituted forms, and metal complexes. Pyrenes include pyrene and other pyrene-based carboxylic acids that can be conjugated using protocols similar to those specified above.

Numerous suitable protecting groups are known in the art for protecting the several functional groups of the compounds of the invention during synthesis. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Protecting groups useful in the context of the present invention include but are not limited to hydroxyl protecting groups such as t-butyldiphenylsilyl, t-butyldimethylsilyl, and dimethoxytrityl groups, thiol protecting groups such as S-trityl, S-p-methoxybenzylthioether, S-p-nitrobenzylthioether, and S-t-butylthioether. (see, e.g., Veber and Hirschmann, et al., *J. Org. Chem.* 1977, 42, 3286 and Atherton, et al., *The Peptides, Gross and Meienhofer*, Eds, Academic Press; New York, 1983; Vol. 9 pp. 1–38).

Other representative protecting groups suitable for practice in the invention may be found in Greene, T. W. and Wuts, P. G. M., "*Protective Groups in Organic Synthesis*" 2d. Ed., Wiley & Sons, 1991.

In one aspect, the present invention is directed to nucleoside monomers that bear at least one conjugate group at the 4'-position. In oligomeric embodiments, the conjugate-bearing nucleoside is the 5'-terminal residue oligomer. In some preferred embodiments the conjugate group is a polyamine, and in other preferred embodiments the conjugate group is a polyether. In further preferred embodiments the conjugate group is a polythioether.

The conjugate groups of the preceding paragraph can further serve as bivalent linkers for other conjugate groups. Thus for instances, a hydroxyl, amino or thiol terminated polyether, polyamine or polythioether is used a linker and the terminal group is then reacted with a suitable functional group on a conjugate molecules to link the conjugate molecule to the polyether, polyamine or polythioether. Suitable functional groups for reacting with hydroxyl, amine or thiol groups include a gamut of groups known in the organic chemical arts including, but not limited to, acid chlorides, anhydrides, cyclic anhydrides, alkyl halides, organometallics, chloroformates, isocynates and the like. In a like manner other terminal groups can be utilized on the linker including, but not limited to, hydrazines, aldehydes, acids, hydroxylamines, semicarbazides, thiosemicarbazides, hydrazones, hydrazides and the like. Protected forms of such compounds can also be used, as for example, protected aldehydes including, C-formyl, o-methylaminobenzenethio, aryl substituted imidazolidino moieties and the like. In a like manner, protected thiol include trityl thiol that can be deblocked allowing a disulfide bonds to be formed between the linker and the a sulfur bearing conjugate group to join the conjugate group to the linker. Various nitrogen linkages can be used to join the conjugate groups including hydrazones, oximes, hydrazide-hydrazone, semicarbazone and semithiocarbazones.

The phrase polyamine species, including polyamines, as used herein refers to species that have a plurality of nitrogen atoms thereon. Polyamines include primary amines, hydrazines, semicarbazines, thiosemicarbazines and similar nitrogenous species. Such species can be symmetrical species such as polyamine containing polymers or they can be unsymmetrical wherein the amine functionalities of the polyamine are separated in space by different moieties. In addition to carbon atoms other atomic species such as nitrogen and sulfur may also be incorporated into the polyamine species. In some preferred embodiments of the invention, at least one nitrogen atom of the polyamine has a free electron pair.

Preferred as polyamine species are species that range in length from about 3 to about 20 units. More preferably species having at least one nitrogen atom and are of the general formula $H_2N[(CH_2)_n-(NH)_y]_t-$ wherein n is an integer between 2 and 8 and t is an integer between 1 and 10. These species can be linear or cyclic. Cyclic amines would include crown amines and mixed crown amines/crown ethers.

Other suitable nitrogen-containing compounds suitable for the formation of polyamine species include $C_1-C_{20}$ straight chain alkylamine, $C_1-C_{20}$ straight chain substituted alkylamine, $C_2-C_{50}$ branched chain alkylamine, $C_2-C_{50}$ branched chain substituted alkylamine, $C_3-C_{50}$ cyclic alkylamine, $C_3-C_{50}$ cyclic substituted alkylamine, $C_2-C_{20}$ straight chain alkenylamine, $C_2-C_{20}$ straight chain substituted alkenylamine, $C_3-C_{50}$ branched chain alkenylamine, $C_3-C_{50}$ branched chain substituted alkenylamine, $C_3-C_{50}$ cyclic alkenylamine, $C_3-C_{50}$ cyclic substituted alkenylamine, $C_2-C_{20}$ straight chain alkynylamine, $C_2-C_{20}$ straight chain substituted alkynylamine, $C_3-C_{50}$ branched chain alkynylamine, $C_3-C_{50}$ branched chain substituted alkynylamine, $C_3-C_{50}$ cyclic alkynylamine, $C_3-C_{50}$ cyclic substituted alkynylamine, $C_1-C_{20}$ straight chain alkylhydrazine, $C_1-C_{50}$ straight chain substituted alkylhydrazine, $C_2-C_{50}$ branched chain alkylhydrazine, $C_2-C_{50}$ branched chain substituted alkylhydrazine, $C_3-C_{50}$ cyclic hydrazoalkane, $C_3-C_{50}$ cyclic substituted hydrazoalkane, $C_2-C_{20}$ straight chain alkenylhydrazine, $C_2-C_{20}$ straight chain substituted alkenylhydrazine, $C_3-C_{50}$ branched chain alkenylhydrazine, $C_3-C_{50}$ branched chain substituted alkenylhydrazine, $C_3-C_{50}$ cyclic hydrazoalkene, $C_3-C_{50}$ cyclic substituted hydrazoalkene, $C_2-C_{20}$ straight chain alkynylhydrazine, $C_2-C_{20}$ straight chain substituted alkynylhydrazine, $C_3-C_{50}$ branched chain alkynylhydrazine, $C_3-C_{50}$ branched chain substituted alkynylhydrazine, $C_3-C_{50}$ cyclic hydrazoalkyne, $C_3-C_{50}$ cyclic substituted hydrazoalkyne, $C_1-C_{20}$ straight chain alkylhydroxyamine, $C_1-C_{20}$ straight chain substituted alkylhydroxyamine, $C_2-C_{50}$ branched chain alkylhydroxyamine, $C_2-C_{50}$ branched chain substituted alkylhydroxyamine, $C_3-C_{50}$ cyclic oxyalkylamine, $C_3-C_{50}$ cyclic substituted oxyalkylamine, $C_2-C_{20}$ straight chain alkenylhydroxyamine, $C_2-C_{20}$ straight chain substituted alkenylhydroxyamine, $C_3-C_{50}$ branched chain alkenylhydroxyamine, $C_3-C_{50}$ branched chain substituted alkenylhydroxyamine, $C_3-C_{50}$ cyclic oxyalkenylamine, $C_3-C_{50}$ cyclic substituted oxyalkenylamine, $C_2-C_{20}$ straight chain alkynylhydroxyamine, $C_2-C_{20}$ straight chain substituted alkynylhydroxyamine, $C_3-C_{50}$ branched chain alkynylhydroxyamine, $C_3-C_{50}$ branched chain substituted alkynylhydroxyamine, $C_3-C_{50}$ cyclic oxyalkynylamine, $C_3-C_{50}$ cyclic substituted oxyalkynylamine, $C_1-C_{20}$ straight chain alkylsemicarbazide, $C_1-C_{20}$ straight chain substituted alkylsemicarbazide, $C_2-C_{50}$ branched chain alkylsemicarbazide, $C_2-C_{50}$ branched chain substituted alkylsemicarbazide, $C_3-C_{50}$ cyclic alkylsemicarbazide, $C_3-C_{50}$ cyclic substituted alkylsemicarbazide, $C_2-C_{20}$ straight chain alkenylsemicarbazide, $C_2-C_{20}$ straight chain substituted alkenylsemicarbazide, $C_3-C_{50}$ branched chain alkenylsemicarbazide, $C_3-C_{50}$ branched chain substituted alkenylsemicarbazide, $C_3-C_{50}$ cyclic alkenylsemicarbazide, $C_3-C_{50}$ cyclic substituted alkenylsemicarbazide, $C_2-C_{20}$ straight chain alkynylsemicarbazide, $C_2-C_{20}$ straight chain substituted alkynylsemicarbazide, $C_3-C_{50}$ branched chain alkynylsemicarbazide, $C_3-C_{50}$ branched chain substituted alkynylsemicarbazide, $C_3-C_{50}$ cyclic alkynylsemicarbazide, $C_3-C_{50}$ cyclic substituted alkynylsemicarbazide, $C_1-C_{20}$ straight chain alkylthiosemicarbazide, $C_1-C_{50}$ straight chain substituted alkylthiosemicarbazide, $C_2-C_{50}$ branched chain alkylthiosemicarbazide, $C_2-C_{50}$ branched chain substituted alkylthiosemicarbazide, $C_3-C_{50}$ cyclic alkylthiosemicarbazide, $C_3-C_{50}$ cyclic substituted alkylthiosemicarbazide, $C_2-C_{20}$ straight chain alkenylthiosemicarbazide, $C_2-C_{20}$ straight chain substituted alkenylthiosemicarbazide, $C_3-C_{50}$ branched chain alkenylthiosemicarbazide, $C_3-C_{50}$ branched chain substituted alkenylthiosemicarbazide, $C_3-C_{50}$ cyclic alkenylthiosemicarbazide, $C_3-C_{50}$ cyclic substituted alkenylthiosemicarbazide, $C_2-C_{20}$ straight chain alkynylthiosemicarbazide, $C_2-C_{20}$ straight chain substituted alkynylthiosemicarbazide, $C_3-C_{50}$ branched chain alkynylthiosemicarbazide, $C_3-C_{50}$ branched chain substituted alkynylthiosemicarbazide, $C_3-C_{50}$ cyclic alkynylthiosemicarbazide, $C_3-C_{50}$ cyclic substituted alkynylthiosemicarbazide, $C_1-C_{20}$ straight chain alkylhydrazone, $C_1-C_{20}$ straight chain substituted alkylhydrazone, $C_2-C_{50}$ branched chain alkylhydrazone, $C_2-C_{50}$ branched chain substituted alkylhydrazone, $C_3-C_{50}$ cyclic hydrazoalkane, $C_3-C_{50}$ cyclic substituted hydrazoalkane, $C_2-C_{20}$ straight chain alkenylhydrazone, $C_2-C_{20}$ straight chain substituted alkenylhydrazone, $C_3-C_{50}$ branched chain alkenylhydrazone, $C_3-C_{50}$ branched chain substituted alkenylhydrazone, $C_3-C_{50}$ cyclic hydrazoalkene, $C_3-C_{50}$ cyclic substituted hydrazoalkene, $C_2-C_{20}$ straight chain alkynylhydrazone, $C_2-C_{20}$ straight chain substituted alkynylhydrazone, $C_3-C_{50}$ branched chain alkynylhydrazone, $C_3-C_{50}$ branched chain substituted alkynylhydrazone, $C_3-C_{50}$ cyclic hydrazoalkyne, $C_3-C_{50}$ cyclic substituted hydrazoalkyne, $C_1-C_{20}$ straight chain alkylhydrazide, $C_1-C_{20}$ straight chain substituted alkylhydrazide, $C_3-C_{50}$ branched chain alkylhydrazide, $C_3-C_{50}$ branched chain substituted alkylhydrazide, $C_3-C_{50}$ cyclic alkylhydrazide, $C_3-C_{50}$ cyclic substituted alkylhydrazide, $C_2-C_{20}$ straight chain alkenylhydrazide, $C_2-C_{20}$ straight chain substituted alkenylhydrazide, $C_3-C_{50}$ branched chain alkenylhydrazide, $C_3-C_{50}$ branched chain substituted alkenylhydrazide, $C_3-C_{50}$ cyclic alkenylhydrazide, $C_3-C_{50}$ cyclic substituted alkenylhydrazide, $C_2-C_{20}$ straight chain alkynylhydrazide, $C_2-C_{20}$ straight chain substituted alkynylhydrazide, $C_3-C_{50}$ branched chain alkynylhydrazide, $C_3-C_{50}$ branched chain substituted alkynylhydrazide, $C_3-C_{50}$ cyclic alkynylhydrazide and $C_3-C_{50}$ cyclic substituted alkynylhydrazide.

As noted above, the conjugate groups of the invention may be attached to the 4'-position of the nucleosidic sugar via a linker. Further linking groups include Ω-aminoalkoxy moieties and Ω-aminoalkylamino moieties for linking a conjugate group to a 4'-hydroxyl group. Many other linking groups are known including many that are commercially available, including heterobifunctional and homobifunctional linking moieties available from the Pierce Co. (Rockford, Ill.).

A further preferred group of linking groups include those groups used as the internucleoside linkages between 4'-desmethyl nucleosides of the parent application, application Ser. No. 039,846, filed Mar. 30, 1993, the entire contents of which are herein expressed incorporated by reference.

In one embodiment for attaching a conjugate molecule to a 4-desmethyl nucleoside, a linking moiety located on a 4-desmethyl nucleoside compound of the invention may be reacted with an active ester derivative of a conjugation moiety of the invention (e.g., cholic acid). Such linking moieties are particularly useful in extending polyalkylamine moieties extending from the oligomeric compounds of the invention. Active ester derivatives are well known to those skilled in the art. Representative active esters include N-hydroxysuccinimide esters, tetrafluorophenolic esters, pentafluorophenolic esters and pentachlorophenolic esters. For cholic acid, the reaction of a pendant amino group and the active ester produces an oligomer in which cholic acid is attached to the N-terminal position through a linking group. Cholic acid or other such pendent groups can be attached to the carboxy terminal of the oligomeric compound by conversion to the N-hydroxysuccinimide ester thereof, and then by further reaction with the oligomeric compound of interest.

Conjugate molecules of the invention can also be directly connected to the 4'-desmethyl nucleosides compounds of the invention without use of linkers. As for instance a conjugate molecule bearing a hydroxyl group, a thiol group, or an amino group is reacted with a 4'-desmethyl nucleoside compound of the invention that has a leaving group at the 4' position. The OH, SH or $NH_2$ moiety of the conjugate groups displaces the leaving group to directly join the conjugate to the 4'-desmethyl nucleoside compound of the invention.

The oligomeric compounds of the invention are synthesized utilizing at least two different methods, both of which can use art recognized solid state synthesis or solution phase synthesis. In a first process, the "4-desmethyl" nucleoside that is to be functionalized with a conjugate group can be attached to a growing oligomeric compound and then so functionalized. In a second process the 4'-desmethyl nucleoside monomer can be first functionalized and then attached to the remainder of the oligomeric compound.

A conjugate group of a compound of the invention can be linked to a 4'-desmethyl nucleoside monomer or oligomer through displacement of a leaving group from the 4'-position (as numbered using the sugar ring numbering of a pentofuranosyl nucleoside) of a nucleoside, or the 4'-terminal position (as numbered using the sugar ring numbering of a pentofuranosyl nucleoside) of an oligonucleoside. In preferred embodiments, the 4'-desmethyl compound has structure:

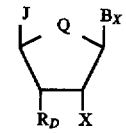

where J is a leaving group. Leaving groups are functional moieties which are designed to be easily displaced. Representative leaving groups include alkyl and arylsulfonyls including p-toluenesulfonyl (tosyl), 4-dimethylaminoazobenzenesulfonyl (dabsyl), 5-dimethylaminonaphthalenesulfonyl (dansyl), trifluoromethylsulfonyl (triflate), methylsulfonyl (mesyl); halogens; o-trichloroacetimidates; 2,4,6-trichlorophenyl; dialkyl phosphite and acyloxy leaving groups including acetoxy, benzoyloxy, p-methoxybenzoyloxy and p-methylbenzoyloxy and other known leaving groups. Acyloxy leaving groups (—$OR_E$ where $R_E$ is C(O)—) are preferred, particularly $OC(O)CH_3$.

$R_D$ can be H, hydroxyl, a nucleoside, an activated nucleotide, a nucleotide, an oligonucleotide or an oligonucleoside or a protected derivative thereof.

$B_X$ is a naturally occurring or non-naturally occurring heterocyclic base as described supra, and also includes such bases bearing protecting groups.

The leaving group can be attached above or below the plane of the sugar ring, i.e., cis or trans to the heretocyclic base. The leaving group may therefore be displaced by either a bimolecular or unimolecular mechanism, dependent upon the specific leaving group and reaction conditions employed. In preferred embodiments the leaving group is trans to the hetrocyclic base, and is displaced via a bimolecular nucleophilic displacement.

In preferred methods of the invention compounds having the above noted structure can be incorporated into a wide variety of oligomeric compounds by standard chemistries. Thus, $R_D$ can be an activated phosphorous group. In the context of the invention activated phosphorous groups are groups which are used to facilitate the creation of internucleosidic bonds in nucleic acid synthetic regimes. Thus, activated phosphorous groups include phosphate groups having $P^V$ such as, for example, activated phosphate esters, and phosphite groups having $P^{III}$ such as phosphoramidites or H-phosphonates. An activated nucleotide according to the invention is a nucleoside which bears an activated phosphorous group.

In preferred processes of the invention a compound of the above structure is incorporated as the terminal nucleoside unit of a preformed oligomeric structure. Such oligomeric structures can be any of the various natural or synthetic oligonucleotides or oligonuleotide mimics as known in the art.

In accordance with the present invention, methods which are amenable to automated synthetic schemes, especially solid-state support synthetic schemes, are preferred. While a number of methodologies can be employed, one preferred methodology follows. A nucleoside analog is attached to a solid support in any conventional fashion. It is customary, and preferred, to employ a linker to a solid support such as a polymeric carrier at the 3' position. An oligonucleotide or oligonucleoside is then synthesized as per any of the various known solid state technologies. A final 4'-desmethyl nucleotide is then added to the growing oligomeric compound.

In one process of the invention, the 4'-desmethyl nucleotide is substituted in the 4'-position with leaving group J as described above. The leaving group is then displaced with a linker or directly with a conjugate group of interest. If a linker is utilized the conjugate group is then attached to the linker, either while still on the solid support or post removal from the solid support.

Alternately the 4'-desmethyl nucleotide is first reacted with a linker or directly with a conjugate group. The modified nucleotide is then attached to the growing oligomeric compound on the solid support.

The 4'-desmethyl nucleoside (or nucleotide) is prepared with any base or base analog, $B_x$, and either a pentofuranosyl moiety, where Q is oxygen, a cyclopentane moiety or fluorinated analogue thereof where Q is $CH_2$, CHF or $CF_2$ or a 4'-deoxy-4'-thio moiety, where Q is S. In certain preferred embodiments of the invention, the nucleoside is a ribonucleoside having a 2'-hydroxyl functionality. Such a functionality can be any of various 2'-groups known in the art. If the 2' functionality is OH (a normal ribonucleotide), the 2'-hydroxyl groups can be protected as necessary by means well known to persons of ordinary skill in the art. The only requirement for this group and for its protection is that the same be designed so as to not interfere with substantive reactions in accordance with this invention. In other preferred embodiments, the 2'-hydroxyl group will be replaced with other functional groups as for example 2'-alkoxy groups, 2'-alkoxy groups that are substituted with other groups including imidazole and other heterocyclic and amino groups, 2'-halogen, particularly fluoro. Particularly useful 2'-O-substituent groups include 2'-aminopropoxy, 2'-imidazoylbutoxy, 2'-methoxy, 2'-ethoxy, 2'-propoxy, 2'-methoxyethoxy and 2'-deoxy-2'-fluoro.

Additional objects, advantages, and novel features of this invention will become apparent to those skilled in the art upon examination of the following examples thereof, which are not intended to be limiting.

EXAMPLE 1

5'-O-tert-Butyldiphenylsilylthymidine, 2.

A stirring solution of thymidine (50.0 g, 207 mmol) and DMAP (10 mg, $8.2 \times 10^{-2}$ mmol) in 400 mL of pyridine was treated with TBDPSCl (43.4 g, 248 mmol) at 25° C. for 16 h. The solvent was removed under reduced pressure and the residue was diluted with 1 L of AcOEt. The mixture was washed with 5% aqueous HCl (2×100 mL) and $H_2O$ (100 mL). The organic layer was dried ($MgSO_4$) and concentrated under reduced pressure. The product was purified by silica gel chromatography ($CH_2Cl_2$/MeOH 20:1) to give 87.3 g (88%) of 2 as a white solid. An analytical sample was crystallized from diethylether. mp 164°–166° C. (170°–171° C. per Matulic-Adamic, *J. Chem. Soc., Chem. Comm.* 1985, 21, 1535) $R_f(CH_2Cl_2$/MeOH 10:1) 0.31. $^1$H-NMR ($CDCl_3$): 1.08 (s, 9H, C-Me$_3$), 1.61 (s, 3H, 5-Me), 2.18 (ddd, 1H, J=13.8, 8.5, 6.0 Hz, 2'H$_\beta$), 2.19 (br, s, 1H, $D_2O$ exchangeable, 3'-OH), 2.44 (ddd, 1H, J=13.8, 5.6, 2.1 Hz, 2'-H$_\alpha$), 3.25 (br s, 1H, 5'-OH, $D_2O$ exchangeable), 3.85 (dd, 1H, J=11.5, 2.5 Hz, 5'-CHH), 3.98 (dd, 1H J=11.5, 2.3 Hz, 5'-CHH), 4.06 (dd, 1H, J=2.5, 2.3 Hz, 4'H), 4.55 (dd, 1H J=6.0, 5.6 Hz, 3'-H), 6.43 (dd, 1H, J=8.5, 5.6 Hz, 1'-H), 7.26–7.51 (m, 6H, aromatic-H), 7.64–7.68 (m, 5H, 6-H and aromatic-H), 9.57 (s, 1H, NH, $D_2O$ exchangeable).

EXAMPLE 2

$N^3$-Benzyloxymethyl-5'-O-tert-butyldiphenylsilylthymidine, 3.

To a stirred solution of 2 (117.0 g, 243.8 mmol) and Hunig's base (diisopropylethylamine 63.0 g, 487.5 mmol) in $CH_2Cl_2$ (400 mL) at 23° C. was added a solution of benzyl chloromethyl ether (40.7 g, 260.0 mmol) over a 15 min. period. The resultant mixture was maintained at 23° C. and stirred for 14 h. Ether (1 L) was added to the mixture and the ethereal solution was washed with 10% aqueous HC (2×100 mL) and $H_2O$ (200 mL). The organic layer was dried ($MgSO_4$) and concentrated under reduced pressure. The residue was purified by silica gel column chromatography ($CH_2Cl_2$/AcOEt 40:1 then 10:1) to yield 128.9 g (88%) of 3 as a white solid. $R_f(CH_2Cl_2$/AcOEt 10:1) 0.31. $^1$H-NMR ($CDCl_3$): 1.10 (s, 9H, C-Me$_3$), 1.65 (s, 3H, 5-Me), 2.16 (m, 1H, 2'-H$_\beta$), 2.41 (m, 1H, 2'-H$_\beta$), 2.53 (br s, 1H 3'-OH), 3.84 (d, 1H, J=8.8 Hz, 5'-CHH), 3.98 (d, 1H, J=8.8 Hz, 5'-CH H), 4.01 (s, 1H, 4'-H), 6.64 (br s, 1H, 3'-H), 4.70 (s, 2H, OCH$_2$Ph), 5.50 (s, 2H, NCH$_2$O), 6.41 (dd, 1H, J=8.0, 5.8 Hz, 1'-H), 7.20–7.50 (m, 13H, aromatic-H), 7.65–7.69 (m, 3H, 6-H and aromatic-H). $^{13}$C-NMR ($CDCl_3$): 12.86 (-5-CH$_3$), 19.45 (+, C-Me$_3$), 27.09 (-, C-Me$_3$), 41.16 (+, 2'-C), 64.25 (+, 5'-C), 70.70 (+, O—C-Ph), 71.97 (-, 4'-C), 72.29 (+, N—C—O), 85.51 (-, 3'-C), 87.20 (-, 1'-C), 110.47 (+, 5-C), 127.72, 128.08, 128.36 (-, aromatic-C), 130.25 (-, 6-C), 132.42, 133.00 (+, aromatic-C) 134.39, 135.37, 135.62 (-, aromatic-C), 137.95 (+, aromatic-C), 151.01 (+, 2-C), 163.68 (+, 4-C).

EXAMPLE 3

$N^3$-Benzyloxymethyl-3'-O-benzoyl-5'-O-tert-butyldiphenylsilyl-thymidine, 4.

A stirred solution of 3 (128.0 g, 213.3 mmol) in a 4:1 mixture of $CH_2Cl_2/Et_3N$ (500 mL) was treated with (48.4 g, 40 mL, 344.6 mmol) of BzCl at 23° C. for 8 h. The resultant precipitate was removed by filtration. The filtrate was concentrated under reduced pressure to leave the crude product as a brownish syrup. Purification of the syrup by silica gel column chromatography (hexanes/AcOEt 10:1 then 1:1) gave 130.7 g (87%) of 4 as a white solid. $R_f$(Hexanes/AcOEt 1:1) 0.82 $^1$H-NMR ($CDCl_3$): 1.40 (s, 9H, C-Me$_3$), 1.60 (s, 3H, 5-Me), 2.37 (ddd, 1H, J=13.8, 9.3, 7.2 Hz, 2'-H$_\beta$), 2.62 (dd, 1H, J=13.8, 4.3 Hz, 2'-H$_\beta$), 4.09 (m, 2H, 5'-H), 4.26 (m, 1H, 4'-H), 4.74 (s, 2H, O—CH$_2$-Ph), 5.54 (s, 2H, N—CH$_2$—O), 5.71 (d, 1H, J=7.2 Hz, 3'-H), 6.57 (dd, 1H, J=9.3, 4.3 Hz, 1'-H), 7.24–7.74 (m, 13H, aromatic-H), 8.05–8.15 (m, 3H, 6-H and aromatic-H). $^{13}$C-NMR ($CDCl_3$): 12.82 (-, 5-Me), 19.54 (+, $\underline{C}$-Me$_3$), 27.16 ($\underline{C}$-$\underline{Me}_3$), 38.28 (+, 2'-C), 64.41 (+, 5'-C), 70.80 (+, O—C—Ph), 72.29 (+, N—C—O), 75.60 (−, 4'-C), 85.28 (−, 1'-C and 3'-C), 110.95 (+, 5-C), 127.72, 128.23, 128.37, 128.50, 128.63 (−, aromatic-C), 129.43 (+, aromatic-C), 129.84, 130.22 (−, aromatic-C), 132.14, 133.07 (+, aromatic-C), 133.60 (−, 6-C), 133.94, 135.32, 135.65 (−, aromatic-C), 138.15 (+, aromatic-C), 151.19 (+, 2-C), 163.50 (+, 4-C), 166.11 (+, benzoyl C=O).

EXAMPLE 4

N$^3$-Benzyloxymethyl-3'-O-benzoylthymidine, 5.

The silyl ether 4 (96.0 g, 136.4 mmol) in THF (600 mL) was treated with hydrogen fluoride-pyridine (70% HF in pyridine, 30 mL) at 0° C. for 4 h under a N$_2$ atmosphere. The resultant mixture was diluted with AcOEt (600 mL) and washed with H$_2$O (2×300 mL). The organic layer was dried (MgSO$_4$) and concentrated at reduced pressure. The residue was purified by silica gel column chromatography (CH$_2$Cl$_2$/AcOEt 10:1) to give 61.6 g (97%) of 5 as a white solid. R$_f$(CH$_2$Cl$_2$/AcOEt 10:1) 0.29. $^1$H-NMR(CDCl$_3$+D$_2$O): 1.95 (s, 3H, 5-Me), 2.53 (m, 2H, 2'-H), 4.00 (m, 2H, 5'-H), 4.25 (m, 1H, 4'-H), 4.71 (s, 2H, O—CH$_2$-Ph), 5.51 (s, 2H, N—CH$_2$-O), 5.60 (m, 1H 3'-H), 6.36 (dd, 1H, J=7.6, 6.6 Hz, 1'-H), 7.25–7.66 (m, 9H, 6-H and aromatic-H), 8.05 (d, 2H, J=7.1 Hz, aromatic-H). $^{13}$C-NMR(CDCl$_3$): 13.29 (−, 5-Me), 37.82 (+, 2'-C), 62.54 (+, 5'-C), 70.73 (+, O—C-Ph), 72.25 (+, N—C—O), 75.82 (−, 4'-C), 85.43 (−, 3'-C), 86.13 (−, 1'-C), 110.41 (+, 5-C), 127.65, 128.36, 128.59 (−, aromatic-C), 129.34 (+, aromatic-C), 129.69 (−, 6-C), 133.60, 135.40 (−, aromatic-C), 137.87 (+, aromatic-C), 151.18 (+, 2-C), 163.65 (+, 4-C), 166.11 (+, benzoyl C=O).

EXAMPLE 5 tert-Butyl N$^3$-Benzoxymethyl-3'-O-benzoylthymidine-5'-carboxylate, 6

The reaction was performed as described by Corey and Samuelsson, *J. Org. Chem.* 1984, 49, 4735, for the oxidation of 5'-OH of the uridine derivative to its corresponding 5'-tert-butyl carboxylate. Chromium(VI) oxide (31.4 g, 314.2 mmol) in CH$_2$Cl$_2$ (480 mL) was cooled to 0° C. and then pyridine (49.7 g, 638.4 mmol) in DMF (120 mL) was added dropwise to the reaction mixture (caution: extremely exothermic) over a period of 1 h. The mixture was stirred at 0° C. for 30 min. Alcohol 5 (36.6 g, 78.5 mmol) in CH$_2$Cl$_2$/DMF (4:1 v/v, 100 mL) was added followed by acetic anhydride (64.1 g, 628.4 mmol) and t-BuOH (116.4 g, 1.57 mmol). The resultant mixture was warmed to 23° C. and stirred for 18 h. Ethanol (20 mL) was added to the reaction and the mixture was stirred for additional 15 min. The reaction mixture was poured into AcOEt (400 mL) and the insoluble material was filtrated through a Buchner funnel padded with 200 g of silica gel and 50 g of MgSO$_4$. The solid left in the funnel was rinsed with AcOEt (4×100 mL). The combined filtrate and rinses were concentrated under reduced pressure. The residue was purified by silica gel column chromatography (hexanes/AcOEt 3:1) to give 25.6 g (61%) of 5 as a white solid. An analytical sample (about 400 mg) was crystallized from ether/hexanes afforded white, needle-like crystals. mp 80°–82° C. R$_f$(hexanes/AcOEt 3:1) 0.23. $^1$H-NMR(CDCl$_3$): 1.55 (s, 9H, C-Me$_3$), 2.21 (ddd, 1H, J=14.3, 9.1, 5.0 Hz, 2'-H$_β$), 2.61 (dd, 1H, J=14.3, 5.2 Hz, 2'-H$_α$), 4.63 (s, 1H, 4'-H), 4.71 (s, 2H, O—CH$_2$-Ph), 5.51 (s, 2H, N—CH$_2$—O), 5.65 (d, 1H, J=5.0 Hz, 3'-H), 6.61 (dd, 1H, J=9.1, 5.2 Hz, 1'-H), 7.24–7.63 (m, 8H, aromatic-H), 8.07 (d, 2H, J=7.1 Hz, aromatic-H), 8.09 (s, 1H, 6-H). $^{13}$C-NMR (CDCl$_3$) : 13.40 (−, 5-Me), 27.92 (−, C-$\underline{Me}_3$), 36.65 (+, 2'-C), 70.58 (+, O—C-Ph), 72.09 (+, N—C—O), 76.66 (−, 4'C), 82.55 (−, 3'-C), 83.36 (+, $\underline{C}$-Me$_3$), 86.88 (−, 1'-C), 110.61 (+, 5-C), 127.55, 127.24 128.23, 128.53 (−, aromatic-C), 128.99 (+, aromatic-C), 129.78 (−, 6-C), 133.71, 134.72 (−, aromatic-C), 138.06 (+, aromatic-C), 151.14 (+, 2-C), 163.28 (+, 4-C), 165.26 (+, benzoyl C=O), 169.40 (+, 5'-C).

EXAMPLE 6

N$^3$-Benzoxylmethyl-3'-O-benzoylthymidine-5'-carboxylic acid, 7.

A solution of 6 (22.0 g, 41.0 mmol) in CF$_3$COOH (100 mL) was stirred at 23° C. for 2 h. Toluene (200 Ml) was then added and the mixture was concentrated under reduced pressure. The coevaporation of toluene was repeated twice to ensure complete removal of the CF$_3$COOH. The resultant light yellow powder was purified by silica gel column chromatography (CH$_2$Cl$_2$/AcOEt 8:1) to afford 19.3 g (87%) of 7 as a white powder. R$_f$(CHCl$_3$/MeOH 4:1) 0.39, $^1$H-NMR (CDCl$_3$+D$_2$O): 1.95 (s, 3H, 5-Me), 2.27 (ddd, 1H, J=14.3, 9.1, 4.9 Hz, 2'-H$_β$), 2.68 (dd, 1H, J=14.3, 5.2 Hz, 2'H$_α$), 4.71 (s, 2H, O—CH$_2$-Ph), 4.79 (s, 1H, 4'-H), 5.52 (s, 2H, N—CH$_2$—O), 5.76 (d, 1H, J=4.9 Hz, 3'-H), 6.55 (dd, 1H, J=9.1, 5.2 Hz, 1'-H), 7.24–7.60 (m, 8H, aromatic-H), 7.97 (s, 1H, 6-H), 8.06 (d, 2H, J=7.1 Hz, aromatic-H). $^{13}$C-NMR(CDCl$_3$): 13.42 (+, 5-Me), 36.68 (+, 2'-C), 70.83 (+, O—C-Ph), 73.38 (+, N—C—O), 76.93 (−, 4'-C), 82.01 (−, 3'-C), 87.58 (−, 1'-C), 110.80 (+, 5-C), 127.72, 127.86, 128.39, 128.70 (−, aromatic-C), 128.71 (+, aromatic-C), 129.90 (−, 6-C), 133.95, 135.63 (−, aromatic-C), 128.53 (+, aromatic-C), 11.20 (+, 2-C), 163.94 (+, 4-C), 165.61 (+, benzoyl C=O), 171.93 (+, 5'-C).

EXAMPLE 7

(2'S,4'S,5'R)-1-[5'-Acetoxy-4'-benzoyloxy-tetrahydrofuran-2'-yl]-N$^3$-benzoxymethylthymine, 8.

A stirred solution of 7 (10.6 g, 22.0 mmol) in DMF (75 mL) was treated with Pb(OAc)$_4$ (11.8 g, 26.5 mmol) at 23° C. for 2 h under darkness. The mixture was diluted with AcOEt (250 mL) and the resultant suspension was filtrated through a Celite pad (50 g). The solid was rinsed several times with AcOEt. The combined filtrate and rinses were concentrated under reduced pressure. The residue was purified by silica gel column chromatography (hexanes/AcOEt 1:1) to give 6.5 g (60%) of a 3:7 α/β (as determined by the $^1$H-NMR 2'-H ratio) anomeric mixture of 8 as a light yellow syrup. An aliquot of the anomeric mixture (~0.2 g) was separated on a silica gel column (hexanes/AcOEt 8:1→2:1 gradient) to afford 53 mg of 8α and 121 mg of 8β, both as white foams.

8α: R$_f$(hexanes/AcOEt, 1:1) 0.53. $^1$H-NMR (CDCl$_3$): 1.95 (d, 3H, J=1.1 Hz, 5-CH$_3$), 2.05 (s, 3H, acetoxy-CH$_3$), 2.52–2.75 (m, 2H, 3'-H), 4.70 (s, 2H, OCH$_2$Ph), 5.49 (s, 2H, NCH$_2$O), 5.60–5.65 (m, 1H, 4'-H), 6.40 (dd, 1H, J=7.9, 3.8 Hz, 2'-H), 6.72 (d, 1H, J=4.0 Hz, 5'-H), 7.06 (d, 1H, J=1.1 Hz, 6-H), 7.22–7.60 (m, 8H, aromatic-H), 8.02 (d, 2H, J=7.6 Hz, aromatic-H). $^{13}$C-NMR (CDCl$_3$): 13.04 (−, 5-CH$_3$), 20.73 (−, acetoxy-CH$_3$), 33.81 (+, 3'-C), 70.45 (+, O—C-Ph), 71.08 (−, 4'-C), 72.11 (+, N—C—O), 85.47 (−, 2'-C), 94.10 (−, 5'-C), 110.90 (+, 5-C), 127.47, 128.11, 128.45 (−, aromatic-C), 128.64 (+, aromatic-C), 129.54 (−, 6-C), 133.55, 133.92 (−, aromatic-C), 137.75 (+, aromatic-C), 150.55 (+, 2-C), 163.01 (+, 4-C), 165.43 (+, benzoyl C=O), 169.18 (+, acetoxy C=O).

Anal. Calcd. for C$_{26}$H$_{26}$N$_2$O$_8$: C, 63.16; H, 5.26; N, 5.67. Found: C, 63.12; H, 5.38; N, 5.45.

8β: $R_f$(hexanes/AcOEt 1:1) 0.47. $^1$H-NMR (CDCl$_3$): 1.95 (s, 3H, 5-CH$_3$), 2.18 (s, 3H, acetoxy-CH$_3$), 2.33 (ddd, 1H, J=14.9, 8.2, 4.9 Hz, 3'-H$_\beta$), 2.75 (dd, 1H, J=14.9, 6.2 Hz, 3'-H$_\alpha$), 4.70 (s, 2H, OCH$_2$Ph), 5.50 (s, 2H, NCH$_2$O), 5.52 (d, 1H, J=4.9 Hz, 4'-H), 6.42 (s, 1H, 5'-H), 6.73 (dd, 1H, J=8.2, 6.2 Hz, 2'-H), 7.22–7.63 (m, 9H, 6-H and aromatic-H), 8.04 (d, 2H, J=7.5 Hz, aromatic-H). $^{13}$C-NMR (CDCl$_3$): 13.40 (−, 5-CH$_3$), 20.82 (−, acetoxy-CH$_3$), 34.95 (+, 3'-C), 70.51 (+, O—C-Ph), 72.07 (+, N—C—O), 76.64 (−, 4'-C), 87.15 (−, 2'-C), 98.61 (−, 5'-C), 111.03 (+, 5-C), 127.45, 128.11, 128.45 (−, aromatic-C), 129.68 (−, 6-C), 133.02, 133.69 (−, aromatic-C), 137.77 (+, aromatic-C), 150.91 (+, 2-C), 162.84 (+, 4-C), 165.12 (+, benzoyl C=O), 169.13 (+, acetoxy C=O). Anal. Calcd for C$_{26}$H$_{26}$N$_2$O$_8$·H$_2$O: C, 60.94; H, 5.47; N, 5.47. Found: C, 60.98; H, 5.18; N, 5.30.

EXAMPLE 8

(2'R,4'S,5'S)-(4'-Benzoxy-5'-O-polyethyleneglycoltetrahydrofuran-2'-yl)-N$^3$-(benzyloxymethyl)thymine (9)

A solution of 3.7 g (7.5 mmol) of acetate 8, 25–35 mmol of PEG alcohol, and 4 mL (3.0 g, 30 mmol) of Et$_3$N in 150 mL of CH$_2$Cl$_2$ was added 14 mL (16.2 g, 75 mmol) of TMSOTf at −23° C. under Ar atmosphere. The reaction mixture was stirred at −23° C. for 2 h, then placed in the freezer (−15° C.) for 16–24 h. The resultant mixture was poured into a 500 mL bilayer mixture of AcOEt/H$_2$O (9:1) containing 15 mL of Et$_3$N. The organic layer was dried (MgSO$_4$) and concentrated at reduced pressure. The residue was purified by SiO$_2$ column chromatography to yield 9.

9a: yield 84.9% (colorless syrup). $R_f$(hexanes/AcOEt 1:1) 0.22. $^1$NMR (CDCl$_3$+D$_2$O) δ1.95 (s, 3H, 5-CH$_3$), 2.34 (ddd, J=14.3, 8.1, 5.1 Hz, 3'-H$_\alpha$), 2.62 (dd, 1H, J=14.3, 6.5 Hz, 3'-H$_\beta$), 3.60–3.95 (m, 4H), 4.70 (s, 2H, OCH$_2$Ph), 5.25 (s, 1H, 5'-H), 5.47 (d, J=5.1 Hz, 4'-H), 5.50 (s, 2H, NCH$_2$O), 6.80 (dd, 1H, J=8.1, 6.5 Hz, 2'-H), 7.18–7.65 (m, 9H, 6-H and aromatic-H), 8.04–8.07 (m, 2H, aromatic-H). $^{13}$C NMR (CDCl$_3$+D$_2$O) δ13.16, 35.00 (3'-C), 61.41, 70.33, 70.76, 72.29, 77.67 (4'-C), 86.53 (2'-C), 106.61 (5'-C), 111.56 (5-C), 127.66, 128.06, 128.33 (6-C), 128.97, 129.84, 133.80, 134.38, 137.99, 151.41 (2-C), 163.35 (4-C), 165.76 (benzoyl C=O).

9b: yield 84.3% (colorless syrup). $R_f$(hexanes/AcOEt 1:1) 0.18. $^1$H NMR (CDCl$_3$) δ1.95 (s, 3H, 5-CH$_3$), 2.34 (ddd, 1H, J=14.7, 8.1, 4.9 Hz, 3'-H$_\alpha$), 2.62 (dd, 1H, J=14.7, 6.3 Hz, 3'-H$_\beta$), 3.36 (s, 3H, CH$_3$O), 3.54–3.98 (m, 12H), 4.72 (s, 2H, OCH$_2$Ph), 5.24 (s, 1H, 5'-H), 5.49 (d, 1H, J=4.9 Hz, 4'-H), 5.52 (s, 2H, NCH$_2$O), 6.80 (dd, 1H, J=8.1, 6.3 Hz, 2'-H), 7.26–7.65 (m, 9H, 6-H and aromatic-H), 8.02–8.06 (m, 2H, aromatic-H). $^{13}$C NMR (CDCl$_3$) δ13.29, 35.06 (3'-C), 59.04 (CH$_3$O), 68.00, 70.14, 70.61, 71.91, 72.19, 77.51 (4'-C), 86.38 (2'-C), 106.43 (5'-C), 111.43 (5-C), 127.65, 128.31, 128.60 (6-C), 129.07, 129.81, 133.70, 134.45, 138.04, 151.41 (2-C), 163.28 (4-C), 165.51 (benzoyl C=O).

9c: 76.5% yield (white foam). $R_f$(hexanes/AcOEt 1:1) 0.05. $^1$H NMR (CDCl$_3$) δ1.98 (s, 3H, 5-CH$_3$), 2.37 (ddd, 1H, J=14.7, 8.2, 4.9 Hz, 3'-H$_\alpha$), 2.62 (dd, 1H, J=14.7, 6.5 Hz, 3'-H$_\beta$), 2.78 (br s, 1H, OH, D$_2$O exchangable), 3.57–3.99 (m, 16 H), 4.72 (s, 2H, OCH$_2$Ph), 5.25 (s, 1H, 5'-H), 5.50 (d, 1H, J=4.9 Hz, 4'-H), 5.52 (s, 2H, NCH$_2$O), 6.80 (dd, 1H, J=8.2, 6.5 Hz, 2'-H), 7.26–7.65 (m, 9H, 6-H and aromatic-H), 8.02–8.06 (m, 2H, aromatic-H). $^{13}$C NMR (CDCl$_3$) δ13.27, 35.02 (3'-C), 61.70, 68.02, 70.15, 70.28, 70.54, 70.73, 72.26, 72.61, 77.61 (4'-C), 86.47 (2'-C), 106.55 (5'-C), 111.40 (5-C), 127.66, 128.31, 128.60 (6-C), 129.12, 129.84, 133.71, 134.48, 138.04, 151.45 (2-C), 163.35 (4-C), 165.61 (benzoyl C=O).

9d: 75.9% yield (yellowish syrup). $R_f$(hexanes/AcOEt 1:1) 0.10. $^1$H NMR (CDCl$_3$) δ1.96 (s, 3H, 5-CH$_3$), 2.34 (ddd, 1H, J=14.7, 7.9, 4.6 Hz, 3'-H$_\alpha$), 2.37 (br s, 1H, OH, D$_2$O exchangable), 2,62 (dd, 1H, J=14.7, 6.8 Hz, 3'-H$_\beta$), 3.44–4.01 (m, 24 H), 4.72 (s, 2H, OCH$_2$Ph), 5.25 (s, 1H, 5'-H), 5.48 (d, 1H, J=4.6 Hz, 4'-H), 5.52 (s, 2H, NCH$_2$O), 6.79 (dd, 1H, J=7.9, 6.8 Hz, 2'-H), 7.25–7.65 (m, 9H, 6-H and aromatic-H), 7.98–8.06 (m, 2H, aromatic-H). $^{13}$C NMR (CDCl$_3$) δ13.03, 34.85 (3'-C), 61.28, 67.83, 70.12, 70.33, 71.38, 71.96, 72.47, 77.44 (4'-C), 86.22 (2'-C), 106.27 (5'-C), 111.08 (5-C), 127.39, 128.08, 128.44 (6-C), 128.94, 129.60, 133.54, 134.38, 137.92, 151.17 (2-C), 163.08 (4-C), 165.29 (benzoyl C=O).

EXAMPLE 9

(2'R,4'S,5'S)-(4'-Hydroxy-5'-O-polyethyleneglycoltetrahydrofuran-2'-yl) thymine (10)

A suspension of 4.5 mmol of 9 and 2–3 g of pd(OH)$_2$/C in 40 mL of 3:1 MeOH /acetone was stirred at 23° C. under H$_2$ atmosphere for 16 h. The suspended material was filtrated through a pad of Celite in a Büchner funnel and the solid in the funnel was rinsed several times with acetone. The combined filtrate and rinses were concentrated at reduced pressure to give a light yellow syrup. The syrup was redissolved in 25 mL of MeOH and 0.3 g (7.5 mmol) of NaOH was added. The mixture was stirred at 23° C. for 6 h and concentrated at reduced pressure. The residue was purifed by SiO$_2$ column chromatography to yield 10.

10a: yield 88.3% (white solid). mp 210° C. (dec.). $R_f$(CHCl$_3$/MeOH 9:1) 0.22. $^1$H NMR (D$_2$O) δ1.84 (s, 3H, 5-CH$_3$), 2.34 (m, 2H, 3'-H), 3.57–3.83 (m, 4H), 4.42 (dd, J=3.7, 2.1 Hz, 4'-H), 5.08 (s, 1H, 5'-H), 6.56 (t, 1H, J=7.1 Hz, 2'-H), 7.56 (s, 1H, 6-H). $^{13}$C NMR (DMSO-d$_6$) δ12.07, 36.94 (3'-C), 59.98, 69.33, 74.11 (4'-C), 84.99 (2'-C), 108.50 (5'-C), 110.43 (5-C), 135.96 (6-C), 150.71 (2-C), 163.67 (4-C). Anal Calcd for C$_{11}$H$_{16}$N$_2$O$_6$·0.7CH$_3$OH: C, 47.69; H, 6.38; N, 9.51. Found: C, 47.70; H, 6.01; N, 9.52.

10b: yield 90.6% (white solid). mp 54°–56° C. $R_f$(CHCl$_3$/MeOH 9:1) 0.41. $^1$H NMR (CDCl$_3$) δ1.93 (s, 3H, 5-CH$_3$), 2.11 (ddd, 1H, J=14.2, 7.9, 4.9 Hz, 3'-H$_\alpha$), 2.33 (br s, 3H, 4'-OH), 2.41 (dd, 1H, J=14.2, 6.5 Hz, 3'-H$_\beta$), 3.38 (s, 3H, CH$_3$O), 3.54–3.94 (m, 12H), 4.37 (d, 1H, J=4.9 Hz, 4'-H), 5.14 (s, 1H, 5'-H), 6.68 (dd, 1H, J=7.9, 6.5 Hz, 2'-H), 7.45 (s, 1H, 6-H), 9.25 (s, 1H, NH). $^{13}$C NMR (CDCl$_3$) δ12.50, 37.42 (3'-C), 58.84 (CH$_3$O), 67.52, 70.25, 70.40, 71.71, 75.01 (4'-C), 85.90 (2'-C), 109.23 (5'-C), 111.60 (5-C), 136.29 (6-C), 151.10 (2-C), 164.40 (4-C). Anal Calcd for C$_{16}$H$_{26}$N$_2$O$_8$·2H$_2$O: C, 46.83; H, 7.32; N, 6.83. Found: C, 46.94; H, 7.50; N, 6.74.

10c: yield 85.9% (white foam). $R_f$(CHCl$_3$/MeOH 9:1) 0.36. $^1$H NMR (CDCl$_3$) δ1.92 (s, 3H, 5-CH$_3$), 2.09 (ddd, 1H, J=14.2, 7.8, 4.9 Hz, 3'-H$_\alpha$), 2.41 (dd, 1H, J=14.2, 6.6 Hz, 3'-H$_\beta$), 3.58–3.90 (m, 16H), 4.36 (d, 1H, J=4.9 Hz, 4'-H), 5.20 (s, 1H, 5'-H), 6.63 (dd, 1H, J=7.8, 6.6 Hz, 2'-H), 7.46 (s, 1H, 6-H), 8.87 (s, 1H, NH). $^{13}$C NMR (CDCl$_3$) δ12.53, 37.35 (3'-C), 61.26, 67.47, 70.00, 70.35, 72.51, 74.99, 77.71 (4'-C), 85.90 (2'-C), 109.27 (5'-C), 111.47 (5-C), 136.33 (6-C), 151.05 (2-C), 164.45 (4-C). Anal Calcd for C$_{17}$H$_{28}$N$_2$O$_9$·0.5 H$_2$O: C, 49.39; H, 7.02; N, 6.78. Found: C, 49.58; H, 7.12; N, 6.66.

10d: yield 87.3% (white wax). $R_f$(CHCl$_3$/MeOH 10:1) 0.40. $^1$H NMR (CDCl$_3$) δ1.92 (s, 3H, 5-CH$_3$), 2.08 (ddd, 1H, J=13.8, 7.7, 4.8 Hz, 3'-H$_\alpha$), 2,39 (dd, 1H, J=13.8, 6.5 Hz, 3'-H$_\beta$), 2.81 (s, 1H, 4'-OH), 3.32–3.92 (m, 24H), 4.01 (s, 1H, OH), 4.37 (d, 1H, J=4.8 Hz, 4'-H), 5.16 (s, 1H, 5'-H), 6.66 (dd, 1H, J=7.8, 6.5 Hz, 2'-H), 7.45 (s, 1H, 6-H), 8.90 (s, 1H, NH). $^{13}$C NMR (CDCl$_3$) δ12.49, 37.50 (3'-C), 61.40, 67.53, 70.14, 70.41, 72.53, 75.01 (4'-C), 85.92 (2'-C), 109.27 (5'-C), 111.50 (5-C), 136.20 (6-C), 151.00 (2-C), 164.25 (4-C). Anal Calcd for C$_{21}$H$_{36}$N$_2$O$_{11}$.0.75 H$_2$O: C, 49.85; H, 7.42; N, 5.54. Found: C, 49.79; H, 7.50; N, 5.60.

EXAMPLE 10

(2'R,4'S,5'S)-(4'-(2-Cyanoethyl-N,N-diisopropylaminophosphorityl)-5'-O-(dimethoxytrityloxytetraethyleneglycol)tetrahydrofuran-2'-yl)thymine (12)

A solution of 1.3 g (3.2 mmol) of 10c, 1.0×10$^{-2}$ g (8.2×10$^{-2}$ mmol) of DMAP, and 1.0 g (10.0 mmol) of Et$_3$N in 30 mL of pyridine was treated with 1.6 g (4.8 mmol) of DMTr-Cl at 23° C. for 14 h. The solvent was removed at reduced pressure and the residue was purified by SiO$_2$ column chromatography (CHCl$_3$/MeOH 20:1 then 10:1) gave 1.9 g (83.6%) of 11 as a yellow foam. R$_f$(CHCl$_3$/MeOH 20:1) 0.23. $^1$H NMR (CDCl$_3$) δ1.92 (s, 3H, 5-CH$_3$), 2.04 (ddd, 1H, J=14.2, 7.6, 4.8 Hz, 3'-H$_\alpha$), 2.32 (dd, 1H, J=14.2, 7.0 Hz, 3'-H$_\beta$), 3.23 (t, 2H, J=5.0 Hz), 3.29 (br s, 1H, 4'-OH), 3.59–3.89 (m, 14H), 3.79 (s, 6H, 2×OCH$_3$), 4.31 (d, 1H, J=4.8 Hz, 4'-H), 5.10 (s, 1H, 5'-H), 6.62 (dd, 1H, J=7.6, 7.0 Hz, 2'-H), 6.82 (d, 4H, J=8.9 Hz), 7.20–7.48 (m, 10H, 6-H and aromatic-H), 8.38 (s, 1H, NH). $^{13}$C NMR (CDCl$_3$) δ12.69, 37.58 (3'-C), 55.26, 63.15, 67.74, 70.73, 75.24 (4'-C), 86.01 (2'-C), 86.08, 109.49 (5'-C), 111.80 (5-C), 113.12, 126.74, 127.68, 127.83, 128.24, 130.13, 136.31 (6-C), 145.13, 151.24 (2-C), 158.41, 164.44 (4-C).

A solution of 1.8 g (2.6 mmol) of 11 and 3×10$^{-2}$ g (1.8×10$^{-1}$ mmol) of N,N-diisopropylammonium tetrazolide in 50 mL of CH$_2$Cl$_2$ was treated with 1.1 g (3.6 mmol) of 2-cyanoethoxy-N,N-diisopropylphosphoramidite at 23° C. for 16 h. The mixture was then diluted with 100 mL CH$_2$Cl$_2$ and washed with sat. aqueous NaHCO$_3$ (30 mL) and brine (30 mL). The organic layer was dried (MgSO$_4$) and concentrated at reduced pressure. The residue was purified by SiO$_2$ column chromatography (0.5% Et$_3$N in AcOEt) gave 1.9 g (77.9%) of 12 as a slightly yellow foam. $^{31}$P NMR (CDCl$_3$) δ149.33 and 149.53 ppm.

EXAMPLE 11

2-(2-Phthalimidoethoxy)ethanol (13)

A suspension of 30.0 g (202.5 mmol) of phthalic anhydride, 20 mL (21.0 g, 199.4 mmol) of 2-(2-aminoethoxy)-ethanol in 400 mL of benzene was added 1.0×10$^{-2}$ g (5.3×10$^{-5}$ mmol) of TsOH.H$_2$O. The reaction flask was connected to a Dean-Stark condenser and then heated to reflux for 14 h. The solvent was removed at reduced pressure and the residue was purified by SiO$_2$ column chromatography (hexanes/AcOEt 1:1 then CHCl$_3$/MeOH 20:1) gave 43.7 g (93.1%) of 13 as a light yellow syrup. This syrup slowly crystallized on standing at room temperature overnight as needle-like crystals. mp 66°–66.5° C. R$_f$(hexanes/AcOEt 1:1) 0.17. $^1$H NMR (CDCl$_3$) d 2.41 (t, 1H, J=6.2 Hz, OH), 3.57–3.93 (m, 8H), 7.69–7.87 (m, 4H). $^{13}$C NMR (CDCl$_3$) d 37.52, 61.62, 68.24, 72.24, 123.36, 131.97, 134.00, 168.38 (C=O). Anal Calcd for C$_{12}$H$_{13}$NO$_4$: C, 61.28; H, 5.53; N, 5.96. Found: C, 61.34; H, 5.62; N, 5.94.

EXAMPLE 12

(2'R,4'S,5'S) -4'-Benzoxy-5'-O-((2-(2-phthalimidoethoxy)-ethyl)-tetrahydrofuran-2'-yl)-N$^3$-(benzoxymethyl)thymine (14)

A solution of 10.8 g (22.0 mmol) of 8, 10.0 g (42.6 mmol) of 13, and 5.7 g (8.0 mL, 57.0 mmol) of Et$_3$N in 200 mL of CH$_2$CL$_2$ was chilled to –23° C. To this solution, 16.9 g (14.6 mL, 76.0 mmol) of TMSOTf was added in one portion. The resultant mixture was stirred at –23° C. for 15 min and then standed in the freezer (–15° C.) for 16 h. The reaction was quenched by pouring into 1 L, 4:1 mixture of AcOEt/H$_2$O containing 20 mL of Et$_3$N. The organic layer was washed with H$_2$O (300 mL), dried (MgSO$_4$), and concentrated at reduced pressure. The residue was purified by SiO$_2$ column chromatography (hexanes/AcOEt 1:1) gave 12.4 g (84.8%) of 14 as very hydroscopic white foam. R$_f$(hexanes/AcOEt 1:1) 0.22. $^1$H NMR (CDCl$_3$) δ1.89 (s, 3H, 5-CH$_3$), 2.30 (ddd, 1H, J=13.2, 8.3, 4.6 Hz, 3'-H$_\alpha$), 2.57 (dd, 1H, J=13.2, 6.5 Hz, 3'-H$_\beta$), 3.63–4.01 (m, 8H), 4.71 (s, 2H, OCH$_2$Ph), 5.19 (s, 1H, 5'-H), 5.36 (d, 1H, J=4.6 Hz, 4'-H), 5.48 (s, 2H, NCH$_2$O), 6.72 (dd, 1H, J=8.3, 6.5 Hz, 2'-H), 7.28–8.01 (m, 13H, 6-H and aromatic-H), 8.02 (dd, 2H, J=7.8, 1.5 Hz, aromatic-H). $^{13}$C NMR (CDCl$_3$) δ13.01 (5-CH$_3$), 34.87 (3'-C), 36.91, 67.64, 67.78, 69.34, 70.62, 72.05, 73.60 (4'-C), 86.30 (2'-C), 106.16 (5'-C), 111.13 (5-C), 123.08, 127.51, 127.76, 128.21, 128.50, 129.20, 129.70, 131.92, 133.54 (6-C), 134.00, 134.41, 138.08, 151.26 (2-C), 163.07 (4-C), 165.29 (phthalimido C=O) 168.02 (benzoxy C=O). Anal Calcd for C$_{36}$H$_{35}$N$_3$O$_{10}$.0.7 CHCl$_3$: C, 58.51; H, 4.74; N, 5.58. Found: C, 58.78; H, 4.74; N, 5.60.

EXAMPLE 13

(2'R,4'S,5'S)-4'-Hydroxy-5'-O-((2-(2-aminoethoxy)ethyl)-tetrahydrofuran-2'-yl)thymine (15)

A suspension of 12.4 g (18.5 mmol) of 14 and 7.6 g of 10% Pd(OH)$_2$/C in 100 mL of 1:1 mixture of acetone/MeOH was stirred under atmosphere H$_2$ for 16 h. The suspended material was filtered through a pad of Celite and the filterate was concentrated at reduced pressure to give 7.8 g (76.7%) of de-BOM product as a white form. The de-BOM product was redissolved in 100 mL MeOH and 1.54 g (48.0 mmol) of H$_2$NNH$_2$ was added. The mixture was heated to reflux for 16 h and then concentrated at reduced pressure. The resultant crude, free amine product (_8 g) was redissolved in 100 mL MeOH and 4.0 g (100.0 mmol) of NaOH was added. The mixture was stirred at 45° C. for 4 h and then the solvent was removed at reduced pressure. The residue was purified by SiO$_2$ column chromatography (2% Et$_3$N in CHCl$_3$/MeOH 1:1) to give 2.2 g (37.7% from 14) of 15 as a white solid. R$_f$(2% Et$_3$N in CHCl$_3$/MeOH 1:1) 0.21. $^1$H NMR (CD$_3$OD) δ1.93 (s, 3H, 5-CH$_3$), 2.27 (m, 2H, 3'-H), 2.82 (m, 2H), 3.58–3.93 (m, 6H), 4.30 (d, 1H, J=4.5 H z, 4'-H), 5.05 (s, 1H, 5'-H), 6.62 (t, 1H, J=8.1 Hz, 2'-H), 7.58 (s, 1H, 6-H). $^{13}$C NMR (CD$_3$OD) δ12.80 (5-CH$_3$), 38.33 (3'-C), 51.23, 68.77, 70.00, 71.31, 76.18 (4'-C), 87.29 (2'-C), 110.77 (5'-C), 112.37 (5-C), 137.84 (6-C), 152.75 (2-C), 166.31 (4-C).

EXAMPLE 14

(2'R,4'S,5'S)-(4'-Hydroxy-5'-O-((2-aminoethoxy)ethyl)-tetrahydrofuran-2'-yl)thymine, cholesterylforamide (16)

A stirred solution of 2.1 g (6.8 mmol) of 15 in 20 mL of 1:1 CH$_2$Cl$_2$/pyridine was added a solution of 3.3 g (7.5 mmol) of cholesteryl chloroformate in 20 mL CH$_2$Cl$_2$ at 0° C. over 45 min period. The resultant mixture was stirred for additional 3 h at 0° C. and then diluted with 200 mL CH$_2$Cl$_2$, washed with sat. aqueous NaHCO₃ (50 mL) and brine (50 mL). The organic layer was dried (MgSO₄) and concentrated at reduced pressure. The residue was purified by SiO₂ column chromatography (CH₂Cl₂/AcOEt 9:1 then AcOEt) to give 2.2 g (45.4%) of 16 as a white solid. $R_f$(AcOEt) 0.44. $^1$H NMR (DMSO-d₆, assignment for some characteristic proton resonances): δ4.93 (s, 1H, 5'-H), 5.33 (d, 1H, J=3.8 Hz, 4'-OH), 5.45 (d, 1H, J=3.8 Hz, 4'-H), 6.48 (t, 1H, J=8.2 Hz, 2'-H), 8.37 (s, 1H, 6-H), 11.38 (s, 1H, NH). $^{13}$C NMR (DMSO-d₆) d 11.65, 12.18, 18.55, 18.98, 22.37, 22.61, 23.38, 23.89, 27.43, 27.83, 31.42, 34.72, 34.87, 35.30, 35,78, 36.10, 41.89, (3'-C), 47.38, 49.56, 55.74, 56.20, 66.82, 69.15, 73.01, 73.88, 74.11 (4'-C), 79.20, 85.09 (2'-C), 108.61 (5'-C), 110.34 (5-C), 139.73 (6-C), 150.67 (2-C), 154.99 (formamide C=O), 163.55 (4-C).

EXAMPLE 15

(2'R,4'S,5'S)-(4'-O-(2-Cyanoethoxy-N,N-diisopropylamino-phosphorityl)-5'-O-((2-aminoethoxy)ethyl)-tetrahydrofuran-2'-yl)thymine, cholesterylforamide (17)

A solution of 1.7 g (2.3 mmol) of 16 and 1.4 g (1.9 mL, 11.0 mmol) of i-Pr₂NEt in 40 mL CH₂Cl₂ was treated with 1.1 g (1.0 mL, 4.6 mmol) of 2-cyanoethyl N,N-diisopropylchlorophosphoramidite at room temperature for 24 h. The resultant mixture was diluted with 100 mL CH₂Cl₂ and washed with sat. aqueous NaHCO₃ (30 mL) and brine (30 mL). The organic layer was dried (MgSO₄) and concentrated at reduced pressure. The residue was purified by SiO₂ column chromatography (0.5% Et₃N in hexanes/AcOEt 1:1 then AcOEt) to give 0.36 g (16.6%) of 17 as a white foam. $^{31}$P NMR (CDCl₃) δ149.23, 149.43 ppm.

A summary of the synthesis of compounds 8 through 17 are presented on the following pages.

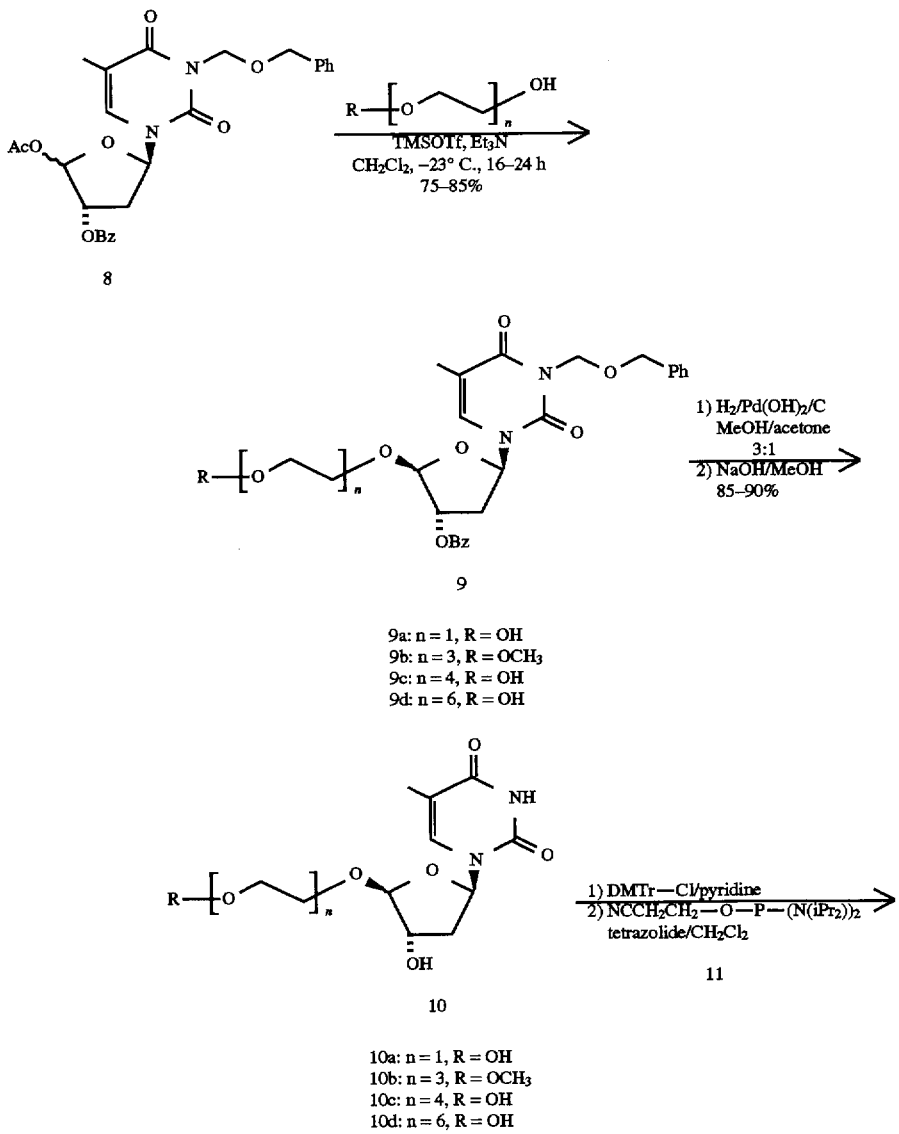

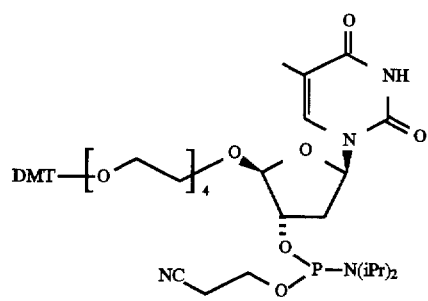
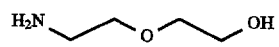
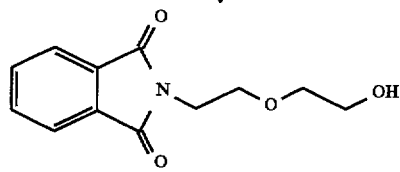
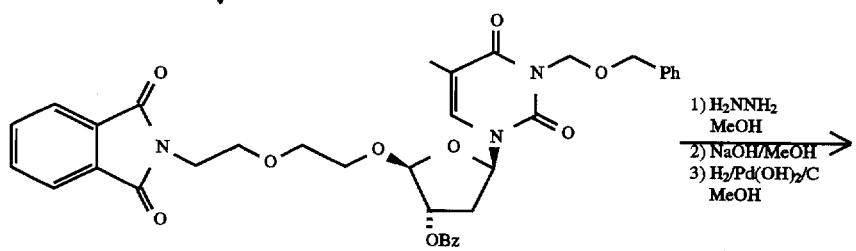
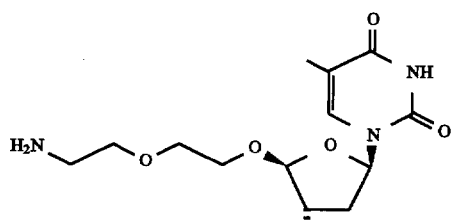
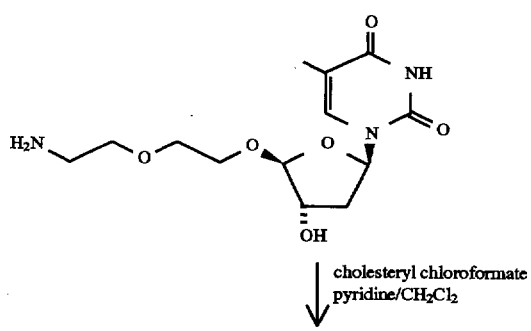

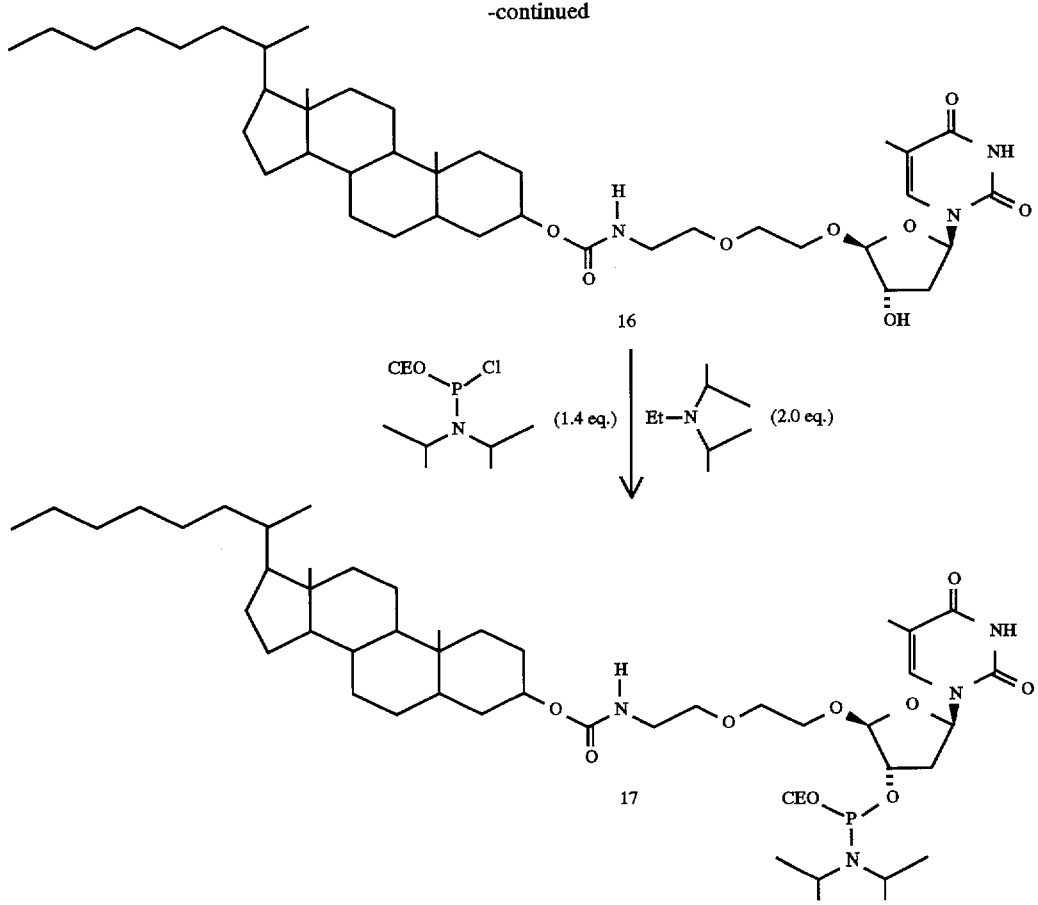

EXAMPLE 16
N³-Benzoxymethyl-(4'-O-benzoyl-5'-O-adamantyl-tetrahydrofuran-2'-yl)thymine (18)

To a solution of 8 (3.5 g, 7.1 mmol) and 1-adamantanol (2.2 g, 14.2 mmol) in CH₂Cl₂ (100 ml) was added TMSOTf (2.7 ml, 3.2 g, 14.2 mmol) at −23° C. in one portion via a syringe. The resultant mixture was stirred at −23° C. for 0.5 hr and then placed in a freezer (−15° C.) for 18 hr. The reaction mixture was then poured into a 40:10:1 bilayer solution of AcOEt/H₂O/Et₃N (500 ml), the organic layer dried over MgSO₄ and concentrated at reduced pressure. The residue was purified by SiO₂ column chromatography (hexanes/AcOEt 4:1 then 2:1) to give 3.6 g (86.7%) of the title compound as a white solid. Rf (hexanes/AcOEt 1:1) 0.60. $^1$H NMR (CDCl₃) δ1.50–1.95 (m, 12H, adamantyl-H), 1.98 (s, 3H, 5-CH₃), 2.05–2.25 (M, 4H, adamantyl-H), 2.3 (ddd, 1H, J=14.5, 7.9, 4.5 Hz, 3'-H$_α$), 2.63 (DD, 1H, J=14.5, 6.5 Hz, 2'-H$_β$), 4.73 (s, 2H, OCH₂Ph), 5.27 (d, 1H, J=4.5 Hz, 4'-H), 5.52 (s, 2H, NCH₂O), 5.61 (s, 1H, 5'-H), 6.71 (dd, 1H, J=7.9, 6.5 Hz, 2'-H), 7.2–7.65 (m, 8H, aromatic-H), 7.78 (s, 1H, 6-H), 8.08 (d, 2H, J=7.6 Hz, aromatic-H). $^{13}$C-NMR (CDCl₃) δ13.37, 30.58, 35.42 (3'-C), 42.66, 45.33, 70.65, 72.20, 75.96, 79.14 (4'-C) 86.31 (2'-C), 99.48 (5'-C), 110.54 (5-C), 127.61, 128.28, 129.25, 129.83, 133.61, 135.36 (6-C), 138.14, 151.37 (2-C), 163.36 (4-C), 165.77 (benzoyl C=O).

EXAMPLE 17
Preparation of Oligonucleotides

Oligonucleotides are prepared utilizing normal protocol for solid state DNA synthesis, (see Oligonucleotide synthesis, a practice approach, Ed. M. J. Gait, IRL Press 1984, Oxford University Press, New York). DMT protected phosphoramidite nucleotides are added to the growing oligonucleotide structure on a solid state support in the normal manner. Coupling efficiencies are typically greater than 96% for each step of the synthesis with the overall coupling efficiency greater than 91% for the oligomer. The resulting oligomers are characterized by both gel chromatography and by HPLC using standard protocols.

EXAMPLE 18
Preparation of Oligonucleotides Containing 5' Terminal Nucleotides Having 4'-Desmethyl Structure Bearing A Conjugation Molecule An oligonucleotide of the desired sequence is prepared as per the preceding Example 17 in the normal 3' to 5' direction. The last nucleotide of the sequence is preformed to include the desired 4'-desmethyl structure bearing a conjugate group, e.g. compounds 12 and 17, attached via linker groups and compound 18, directly attached, thereon as per the above Examples 10, 15 and 17. This last nucleotide unit, as a 3'-phosphoamidite, is coupled to the remainder of the oligonucleotide sequence utilizing normal protocol for solid state DNA synthesis, as above. As with the remainder of the sequences, coupling efficiencies are generally greater than 96% for this step of the synthesis.

A typical synthesis was that of an oligonucleotide of the sequence:

T*GC ATC CCC CAG GCC ACC AT, SEQ ID NO. 1, where T* is the nucleotide of compound 12, compound 17 or compound 18 above. The sequences was synthesizer up to and including the penultimate nucleotide unit. The conjugate group bearing, 4-desmethyl, terminal nucleotide, e.g. compound 12, was then used as the ultimate nucleotide unit. The oligonucleotide was removed from the solid support and purified by HPLC in the standard manner.

EXAMPLE 18

Assay for Separating Expression of Intercellular Adhesion Molecule From Vascular Adhesion Molecules Using Selective Protein Inhibition Various adhesion molecules are known that are associated with certain adverse events in biological systems. The study of these molecules can be compounded by overlapping activities. Since the intercellular adhesion molecule, ICAM-1, and the vascular adhesion molecule, VCAM-1, both are capable of expressing certain similar properties, e.g. cell adhesion or clumping, segregation of certain of their properties, one from the other, would assist in the evaluation of the properties of a singular adhesion molecule. This cellular assay isolates cytokine induced protein induction of ICAM-1 from that of VCAM-1. The assay differentiates specific protein inhibition of ICAM-1 expression from VCAM-1 expression via use of a probe oligonucleotide having a sequence complementary to the ICAM-1 messenger RNA. Inhibition of the induction of ICAM-1 messenger RNA is effected by treatment of the cells with the probe oligonucleotide in presence of a cationic liposome formulation (DOTMA/DOPE). Cells showing positive adhesion molecule expression in response to cytokine treatment are identified by increases in basal levels of the adhesion molecule protein after treatment with a combination of human TNF-α and murine INF-τ using a fluorescence activated cell sorter to identify the cells stained with fluorescent antibodies to either the ICAM-1 or VCAM-1 expressed proteins.

The oligonucleotide utilized as the probe was an oligonucleotide of the invention of the sequence T*GC ATC CCC CAG GCC ACC AT, SEQ ID NO. 1, complementary to the 3' untranslated region of murine ICAM-1 messenger RNA. It includes a conjugation PEG molecule (compound 12 above) as the 5' terminal T nucleotide (nucleotide T* in the above sequence). This oligonucleotide is then used to differentiate ICAM-1 expression from VCAM-1 expression in the test protocol. In cell lines from other species, the base sequence of conjugated oligonucleotide of the invention used in the test is synthesized to be of a sequence complementary to a portion of the ICAM-1 messenger RNA for the species of interest.

A murine endothelioma cell line designated bEND.3, supplied by Dr. Werner Risau, Max-Planck-Institute, Planegg-Martinsreid, Germany, is tested for adhesion molecule expression as follows. The cells were treated with nanomolar concentrations of the conjugated oligonucleotide, SEQ ID NO. 1, in the presence of 15 µg/ml DOTMA/DOPE liposome (Lipofectin) for 4 hours in a serum free media (Opti-MEM serum-free medium, GIBCO, Grand Island, N.Y.) in the manner described by Chiang et al., *J. Biol. Chem.*, 1991, 266, 18162–18171 or Bennett, et al., *J. Immunol*, 1994, 152, 3530–3540. The media was aspirate and adhesion molecule expression was induced with human TNF-α (5 ng/ml, R&D Systems, Minneapolis, Minn.) and murine IFN-τ (1000µ/ml, Genzyme, Cambridge, Mass.) overnight in DMEM high glucose with 10% fetal bovine serum (Hyclone, Logan, Utah). The cells were trypsinized and washed. The cells were stained with ICAM-1-PE fluorescent antibodies (anti-ICAM-lmAB, PharMingen, San Diego, Calif.) and VCAM-1-FITC fluorescent antibodies (anti-VCAM-1 mAB, PharMingen, San Diego, Calif.) and read on a fluorescence activated cell sorter.

Concurrent treatment of the same bEND.3 cell line absent the conjugated oligonucleotide served as a positive control. Both ICAM-1 and VCAM-1 induction were observed in the positive control and normalized to 100%. The conjugated oligonucleotide was used at 0.1, 0.3 and 0.5 uM and the levels of both of induced expression ICAM-1 and VCAM-1 were compared to this positive control. Inhibition of VCAM-1 expression was observed to be 90.08%, 103.82% and 96.33% of control for the 0.1, 0.3 and 0.5 uM concentrations, respectively whereas inhibition of ICAM-1 expression was 3.77%, 4.40% and 8.74% of control for the 0.1, 0.3 and 0.5 uM concentrations, respectively.

As these results show, in the murine bEND.3 cell line both ICAM-1 and VCAM-1 expression were induced in the positive control. However, in the presence of the ICAM-1 specific messenger RNA complementary oligonucleotide of the invention, VCAM-1 protein expression was maintained but ICAM-1 protein expression was inhibited. Thus the expression of VCAM-1 is disconnect from that of ICAM-1 such that VCAM-1 expression can be examined independent of ICAM-1 expression.

What is claimed is:

1. A method for forming a 4'-desmethyl conjugated monomer having structure:

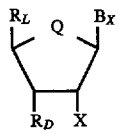

comprising the steps of:

(a) providing a synthon having structure:

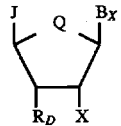

and (b) contacting this synthon with an activated conjugating group;

the contacting being for a time and under reaction conditions sufficient to form the conjugated monomer;

wherein:

$R_L$ is a group of formula:

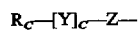

$R_C$ is O-alkyl, O-alkenyl, O-alkynyl, a polyamine, a polyether, a steroid molecule, a reporter molecule, an aromatic lipophilic molecule, a non-aromatic lipophilic molecule, a reporter enzyme, a peptide, a protein, a water soluble vitamin, a lipid soluble vitamin, a carbohydrate, a terpene molecule, a phospholipid, an intercalator, a cell receptor binding molecule, a crosslinking agent, of a porphyrin;

Z is O, S or HN;

Y is a bivalent linker;

e is 0 or 1;

$B_x$ is a nucleobase;

X is H, OH, O-alkyl, O-alkoxylalkyl, O-alkylamino, or F;

J is a leaving group;

Q is O, S, $CH_2$, CHF or $CF_2$; and $R_D$ is H, hydroxyl, an activated phosphorous group, a nucleoside, an activated nucleotide, a nucleotide, an oligonucleotide, an oligonucleoside or a protected derivative thereof.

2. The method of claim 1 wherein J is OH, SH, $NH_2$, trifluoromethylsulfonyl, methylsulfonyl, halogen, O-trichloroacetimidate, acyloxy, dialkyl phosphite, 2,4,6-trichlorophenyl, p-toluenesulfonyl, 4-dimethylaminoazobenzenesulfonyl or 5-dimethylaminonaphthalenesulfonyl.

3. The method of claim 1 wherein J is trifluoromethylsulfonyl, methylsulfonyl, halogen or acyloxy.

4. A method for forming a 4'-desmethyl conjugate oligomer having structure:

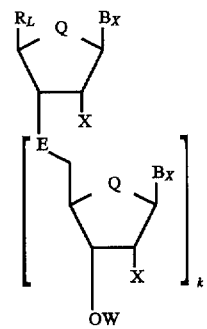

comprising the steps of:

(a) providing a first synthon having structure:

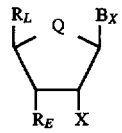

and (b) contacting the first synthon with a second synthon having structure:

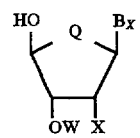

the contacting being for a time and under reaction conditions sufficient to form the conjugated oligomer;

wherein:

$R_L$ is a group of formula:

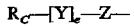

$R_C$ is O-alkyl, O-alkynyl, a polyamine, a polyether, a steroid molecule, a reporter molecule, an aromatic lipophilic molecule, a non-aromatic lipophilic molecule, a reporter enzyme, a peptide, a protein, a water soluble vitamin, a lipid soluble vitamin, a carbohydrate, a terpene molecule, a phospholipid, an intercalator, a cell receptor binding molecule, a crosslinking agent, or a porphyrin;

Z is O, S or HN;

Y is a bivalent linker;

e is 0 or 1;

E is a phosphodiester, phosphorothioate, phosphorodithioate, phosphamidate, alkyl phosphonate or phosphotriester phosphorous linking group;

$R_E$ is an activated phosphorous group;

W is H, a hydroxyl protecting group or a solid state support;

k is an integer from 0 to 50;

$B_x$ is a nucleobase;

X is H, OH, O-alkyl, O-alkoxylalkyl, O-alkylamino, or F; and

Q is O, S, $CH_2$, CMF or $CF_2$.

5. A method for forming an oligonucleotide having a conjugate group thereon comprising the steps (a) selecting an oligonucleotide having a 4'-desmethyl nucleoside at the 5'-terminal position of the oligonucleotide; and (b) linking a conjugate group to said 4'-desmethyl nucleoside, to form said oligonucleotide having said conjugate group thereon.

* * * * *

UNITED STATES PATENT AND TRADEMARK OFFICE
CERTIFICATE OF CORRECTION

PATENT NO. : 5,688,941
DATED : November 18, 1997
INVENTOR(S) : Phillip Dan Cook and Kelly Teng It is certified that error appears in the above-identified patent and that said Letters Patent is hereby corrected as shown below:

Column 8,
Line 37-38, please delete "aster-" and insert therefor -- a ster- --

Signed and Sealed this

Eighteenth Day of December, 2001

Attest:

Attesting Officer

JAMES E. ROGAN
*Director of the United States Patent and Trademark Office*

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 20 bases
( B ) TYPE: nucleic acid
( C ) STRANDEDNESS: single
( D ) TOPOLOGY: linear ( x i ) SEQUENCE DESCRIPTION: SEQ ID NO:1:

TGCATCCCCC AGGCCACCAT     20